United States Patent
Park et al.

(10) Patent No.: US 11,419,561 B2
(45) Date of Patent: Aug. 23, 2022

(54) ADAPTIVE BIO-SIGNAL FEATURE COMBINING APPARATUS AND METHOD

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Dae Geun Jang, Yongin-si (KR); Young Soo Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1264 days.

(21) Appl. No.: 15/856,234

(22) Filed: Dec. 28, 2017

(65) Prior Publication Data

US 2018/0177466 A1 Jun. 28, 2018

(30) Foreign Application Priority Data

Dec. 28, 2016 (KR) .......................... 10-2016-0181373
Dec. 11, 2017 (KR) .......................... 10-2017-0169187

(51) Int. Cl.
*A61B 5/021* (2006.01)
*A61B 5/00* (2006.01)
(Continued)

(52) U.S. Cl.
CPC ............ *A61B 5/7278* (2013.01); *A61B 5/021* (2013.01); *A61B 5/0205* (2013.01);
(Continued)

(58) Field of Classification Search
CPC .............. A61B 5/02108–02125; A61B 5/1102
See application file for complete search history.

(56) References Cited

U.S. PATENT DOCUMENTS 7,282,028 B2  10/2007  Kim et al.
7,333,850 B2  2/2008  Marossero et al.
(Continued)

FOREIGN PATENT DOCUMENTS

CN  103815888 A  5/2014
CN  104274165 A  1/2015
(Continued)

OTHER PUBLICATIONS

Communication dated May 8, 2018, from the European Patent Office in counterpart European Application No. 17210907.6.
(Continued)

*Primary Examiner* — Meredith Weare
(74) *Attorney, Agent, or Firm* — Sughrue Mion, PLLC

(57) ABSTRACT

An adaptive bio-signal feature combining apparatus includes: a feature extractor configured to extract first feature values and second feature values from a bio-signal of an object; a stable interval determiner configured to determine at least one stable interval in the bio-signal; a statistical variable calculator configured to calculate a statistical variable value of a first feature and a statistical variable value of a second feature for each of the at least one stable interval based on the first and second feature values extracted from the at least one stable interval; and a feature combiner configured to calculate an integrated combining coefficient that is used to combine the first feature and the second feature, based on the statistical variable value of the first feature and the statistical variable value of the second feature.

20 Claims, 22 Drawing Sheets

(51) Int. Cl.
  *A61B 5/029* (2006.01)
  *A61B 5/11* (2006.01)
  *A61B 5/026* (2006.01)
  *A61B 5/02* (2006.01)
  *A61B 5/0205* (2006.01)
  *A61B 5/318* (2021.01)
  *A61B 5/389* (2021.01)

(52) U.S. Cl.
  CPC .......... *A61B 5/02007* (2013.01); *A61B 5/029* (2013.01); *A61B 5/02028* (2013.01); *A61B 5/0261* (2013.01); *A61B 5/02108* (2013.01); *A61B 5/1102* (2013.01); *A61B 5/318* (2021.01); *A61B 5/389* (2021.01); *A61B 5/721* (2013.01); *A61B 5/7232* (2013.01); *A61B 5/7239* (2013.01); *A61B 5/7246* (2013.01); *A61B 5/7264* (2013.01); *A61B 5/1118* (2013.01); *A61B 2505/07* (2013.01); *A61B 2562/0219* (2013.01)

(56) References Cited

U.S. PATENT DOCUMENTS

| | | |
|---|---|---|
| 7,485,095 B2 | 2/2009 | Shusterman |
| 8,454,555 B2 | 6/2013 | Struijk et al. |
| 8,620,591 B2 | 12/2013 | Wegerich |
| 9,011,346 B2 | 4/2015 | Wiard et al. |
| 9,101,261 B2 | 8/2015 | Kim et al. |
| 9,241,637 B2 | 1/2016 | Wiard et al. |
| 9,706,931 B2 | 7/2017 | Fuke et al. |
| 9,833,151 B2 | 12/2017 | Wiard et al. |
| 2013/0310700 A1 | 11/2013 | Wiard et al. |
| 2014/0275854 A1 | 9/2014 | Venkatraman et al. |
| 2015/0011913 A1 | 1/2015 | Fuke et al. |
| 2015/0223699 A1 | 8/2015 | Yoon et al. |
| 2015/0282718 A1 | 10/2015 | Wiard et al. |
| 2016/0095522 A1 | 4/2016 | Wiard et al. |
| 2016/0220188 A1 | 8/2016 | Chon et al. |
| 2016/0270668 A1 | 9/2016 | Gil |
| 2017/0360314 A1* | 12/2017 | Proenca ............. A61B 5/02125 |
| 2018/0028080 A1 | 2/2018 | Ouwerkerk et al. |

FOREIGN PATENT DOCUMENTS

| | | | |
|---|---|---|---|
| KR | 10-0397188 B1 | 9/2003 | |
| KR | 10-0455286 B1 | 11/2004 | |
| KR | 10-0657901 B1 | 12/2006 | |
| KR | 10-1141523 B1 | 5/2012 | |
| KR | 10-1236139 B1 | 2/2013 | |
| KR | 10-1503604 B1 | 3/2015 | |
| KR | 10-1596662 B1 | 2/2016 | |
| KR | 10-1629901 B1 | 6/2016 | |
| WO | 2012103296 A2 | 8/2012 | |
| WO | 2016123484 A1 | 8/2016 | |
| WO | 2016135583 A1 | 9/2016 | |
| WO | WO-2016138965 A1 * | 9/2016 | ......... A61B 5/02416 |

OTHER PUBLICATIONS

Sandrine C. Millasseau et al. "Contour analysis of the photoplethysmographic pulse measured at the finger" Journal of Hypertension, Lippincott Williams & Wilkins, Ltd. vol. 24, No. 8, Aug. 1, 2006, (pp. 1449-1456) XP002673731.

Youngzoon Yoon et al., "Nonconstrained Blood Pressure Measurement by Photoplethysmography", Journal of the Optical Society of Korea, vol. 10, No. 2, Jun. 2006, pp. 91-95.

Sandrine C. Millasseau et al., "The Vascular Impact of Aging and Vasoactive Drugs: Comparison of Two Digital Volume Pulse Measurements", Digital Pulse Contour Analysis, American Journal of Hypertension, Ltd., Published by Elsevier Inc., Jun. 2003; vol. 16, No. 6, pp. 467-472.

Communication dated Aug. 3, 2021, issued by the State Intellectual Property Office of P.R. China in counterpart Chinese Application No. 201711463862.8.

* cited by examiner

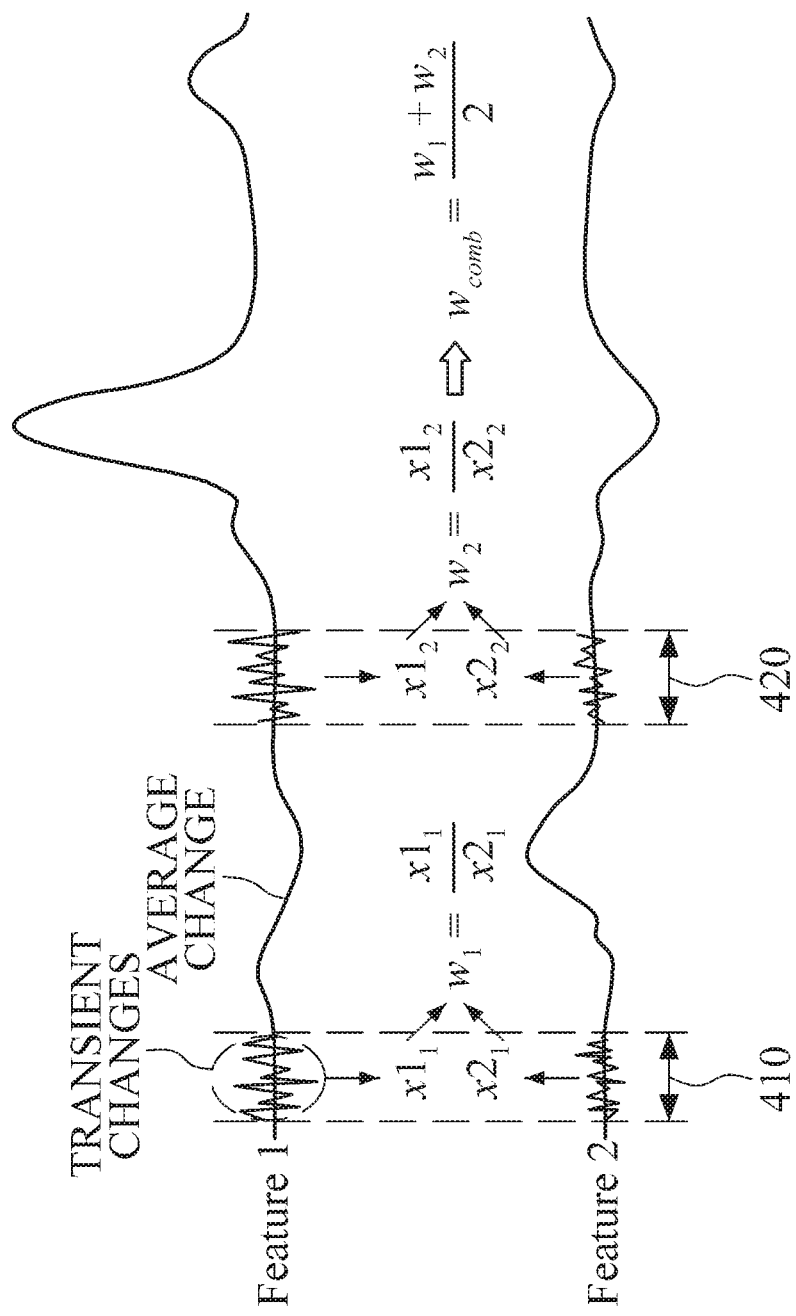

ADAPTIVE BIO-SIGNAL FEATURE COMBINING APPARATUS AND METHOD

CROSS-REFERENCE TO RELATED APPLICATIONS

This application claims priority from Korean Patent Application No. 10-2016-0181373, filed on Dec. 28, 2016, and Korean Patent Application No. 10-2017-0169187, filed on Dec. 11, 2017, in the Korean Intellectual Property Office, the disclosures of which are incorporated herein by reference in their entireties.

BACKGROUND

1. Field

Apparatuses and methods consistent with exemplary embodiments relate to an adaptive bio-signal feature combining apparatus and method.

2. Description of the Related Art

Healthcare technology has attracted much attention due to the rapid entry into an aging society and relevant social problems such as increase in medical expenses. Accordingly, not only medical devices that can be utilized by hospitals and inspection agencies but also small-sized medical devices that can be carried by individuals such as wearable devices are being developed. In addition, such a small-sized medical device is worn by a user in the form of a wearable device capable of directly measuring cardiovascular health status such as blood pressure or the like, so that the user can directly measure and manage cardiovascular health status.

Therefore, recently, studies on a method of estimating a blood pressure by analyzing a bio-signal for minimization of a device have been conducted.

SUMMARY

According to an aspect of an exemplary embodiment, there is provided an adaptive bio-signal feature combining apparatus including: a feature extractor configured to extract first feature values and second feature values from a bio-signal of an object; a stable interval determiner configured to determine at least one stable interval in the bio-signal; a statistical variable calculator configured to calculate a statistical variable value of a first feature and a statistical variable value of a second feature for each of the at least one stable interval based on the first and second feature values extracted from the at least one stable interval; and a feature combiner configured to calculate an integrated combining coefficient that is used to combine the first feature and the second feature, based on the statistical variable value of the first feature and the statistical variable value of the second feature, wherein the feature extractor, the stable interval determiner, the statistical variable calculator, and the feature combiner are included in one or more processors.

The bio-signal may include at least one of an electrocardiogram (ECG) signal, a photoplethysmogram (PPG) signal, an electromyogram (EMG) signal, and a ballistocardiogram (BCG) signal.

The first feature may be related to a cardiac output and the second feature is related to a total peripheral vascular resistance.

The first feature may include at least one of $P_{max}/P_{area}$, $P_{max}/P_3$, $P_{sys}/P_3$, $P_1/P_3$, $P_2/P_3$, and $1/T_{period}$, the second feature may include at least one of $1/(T_3-T_{sys})$, $1/(T_3-T_{max})$, $1/(T_3-T_1)$, $1/(T_3-T_2)$, $P_2/P_1$, and $P_3/P_1$, wherein $T_{period}$ denotes a period of the bio-signal, $T_1$ denotes a time of a peak point of a first component pulse constituting the bio-signal, $P_1$ denotes an amplitude of the bio-signal at $T_1$, $T_2$ denotes a time of a peak point of a second component pulse constituting the bio-signal, $P_2$ denotes an amplitude of the bio-signal at $T_2$, $T_3$ denotes a time of a peak point of a third component pulse constituting the bio-signal, $P_3$ denotes an amplitude of the bio-signal at $T_3$, $T_{max}$ denotes a time of a peak point of the bio-signal in a first interval, $P_{max}$ denotes an amplitude of the bio-signal at $T_{max}$, $T_{sys}$ denotes an intermediate time between $T_1$ and $T_{max}$, an arbitrary internally dividing point between $T_1$ and $T_{max}$, or an arbitrary internally dividing point between $T_1$ and $T_2$, $P_{sys}$ denotes an amplitude of the bio-signal at $T_{sys}$, and $P_{area}$ denotes a sum of amplitudes of the bio-signal in a second interval.

The stable interval determiner may determine the at least one stable interval based on an output value of an acceleration or gyro sensor attached to the object.

The stable interval determiner may compare the output value of the acceleration or gyro sensor at a time of bio-signal measurement with a predetermined threshold value, and, in response to the output value of the acceleration or gyro sensor being maintained less than or equal to the threshold value for a predetermined time period, the stable interval determiner may be further configured to determine that the predetermined time period is a stable interval.

The stable interval determiner may determine the at least one stable interval based on an amount of change in the first feature or second feature extracted from the bio-signal.

The amount of change in the first feature or second feature may be defined as a fluctuation with respect to a mean value of the corresponding first feature or second feature.

The fluctuation may include a variance, a standard deviation, and a mean absolute deviation.

The stable interval determiner may compare the amount of change in the first feature or second feature extracted during a time period with a predetermined threshold value and determine the time period as the stable interval when the amount in change in the first feature or second feature is less than or equal to the predetermined threshold value.

The statistical variable may include a mean, a variance, a standard deviation, and a mean absolute deviation.

The feature combiner may calculate a combining coefficient of each stable interval based on the statistical variable values of the first and second features which are calculated for each stable interval.

The feature combiner may calculate the combining coefficient of each stable interval by dividing the statistical variable value of the first feature of each stable interval by the statistical variable value of the second feature of each stable interval.

The feature combiner may calculate the integrated combining coefficient by arithmetically averaging the combining coefficients calculated for each stable interval.

The feature combiner may calculate the feature combining coefficient by applying different weights to the combining coefficients calculated for each stable interval and linearly combining the combining coefficients to which the different weights are applied.

The feature combiner may apply a higher weight to a combining coefficient of a temporally later stable interval.

The feature combiner may linearly combine the first feature and the second feature based on the calculated integrated combining coefficient.

The adaptive bio-signal feature combining apparatus may further include a controller configured to update the integrated combining coefficient.

The controller may control the feature extractor, the stable interval determiner, the statistical variable calculator, and the feature combiner to update the integrated combining coefficient according to a designated update period.

The controller may control the feature extractor, the stable interval determiner, the statistical variable calculator, and the feature combiner to constantly update the integrated combining coefficient by overlapping the at least one stable interval in a sliding-window scheme.

The adaptive bio-signal feature combining apparatus may further include a joint statistical variable calculator configured to calculate a joint statistical variable value between the first feature and the second feature, wherein the feature combiner calculates the integrated combining coefficient based on the statistical variable value of the first feature, the statistical variable value of the second feature, and the joint statistical variable value.

The joint statistical variable may include a covariance and a correlation coefficient.

According to an aspect of another exemplary embodiment, there is provided an adaptive bio-signal feature combining method including: extracting first feature values and second feature values from a bio-signal of an object; calculating a statistical variable value of a first feature and a statistical variable value of a second feature based on the first feature values and the second feature values which are extracted from at least one stable interval; and calculating an integrated combining coefficient that is used to combine the first feature and the second feature based on the statistical variable values of the first and second features.

According to an aspect of still another exemplary embodiment, there is provided a blood pressure measurement apparatus including: a stable interval determiner configured to determine a stable interval of a bio-signal of an object; a statistical variable calculator configured to calculate a statistical variable value of a first feature and a statistical variable value of a second feature, the first feature and the second feature being extracted from the stable interval of the bio-signal; a feature combiner configured to calculate an integrated combining coefficient based on the statistical variable values of the first and second features and combine the first feature and the second feature based on the calculated integrated combining coefficient; and a blood pressure estimator configured to estimate a blood pressure of the object based on the combined feature, wherein the stable interval determiner, the statistical variable calculator, the feature combiner, and blood pressure estimator are included in one or more processors.

BRIEF DESCRIPTION OF THE DRAWINGS

The above and/or other aspects will be more apparent by describing certain exemplary embodiments, with reference to the accompanying drawings, in which:

FIG. 7B is a diagram for describing the process of obtaining an integrated combining coefficient;

DETAILED DESCRIPTION

Figure 1:
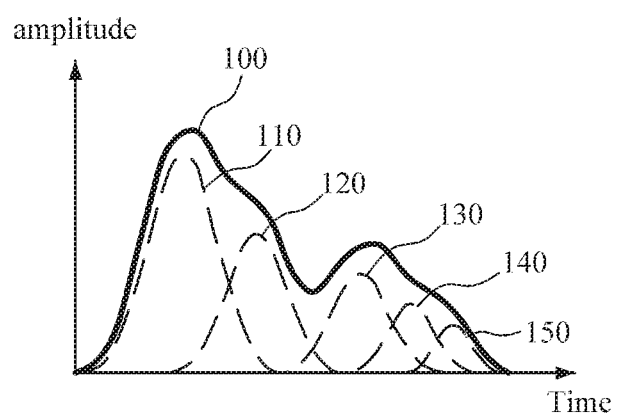
FIG. 1 is a diagram illustrating a bio-signal according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described in below are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

Meanwhile, an apparatus for providing a health status of the cardiovascular system described herein may be implemented as a software module or in the form of a hardware chip and be mounted in an electronic device. In this case, the electronic device may include a mobile phone, a smart phone, a notebook computer, a personal digital assistant (PDA), a portable multimedia player (PMP), a navigation system, an MP3 player, a digital camera, a wearable device, etc., and the wearable device may include various types of wearable devices, such as a wristwatch type, a wristband type, a ring type, a belt-type, a necklace type, an ankle band type, a thigh band type, a forearm band type, and the like. However, the electronic device is not limited to the above mentioned examples, and the wearable device is also not limited to the above-described examples.

FIG. 1 is a diagram illustrating a bio-signal according to an exemplary embodiment. Specifically, FIG. 1 illustrates a photoplethysmogram (PPG) signal.

Referring to FIG. 1, a waveform of a PPG signal 100 may be a summation of a propagation wave 110, which is caused by blood flow and propagates from the heart to peripheral parts of a body, and reflection waves 120 to 150, which is caused by the blood flow and returns from the peripheral parts of the body. In the illustrated example, the PPG signal 100 is a summation of five component pulses 110 to 150.

Change in blood pressure may depend on a cardiac output, which represents the amount of blood ejected by the heart in a unit of time, and a total peripheral vascular resistance. It may be expressed as Equation 1.

$$BP = CO \times TPR \quad (1)$$

Here, BP represents a blood pressure difference between the right and left ventricles, CO represents a cardiac output, and TPR represents a total peripheral vascular resistance.

As the cardiac output or the total peripheral vascular resistance increases, so does the blood pressure. Thus, when a feature related to the cardiac output and a feature related to the total peripheral vascular resistance are extracted from the PPG signal 100 and a feature obtained by adequately combining the two extracted features is used in blood pressure estimation, it may be possible to increase the accuracy in blood pressure estimation.

Figure 2:
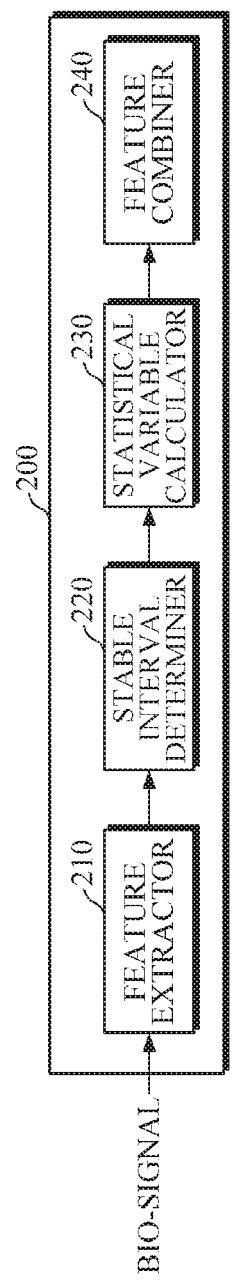
FIG. 2 is a block diagram illustrating an adaptive bio-signal feature combining apparatus according to an exemplary embodiment.

FIG. 2 is a block diagram illustrating an adaptive bio-signal feature combining apparatus according to an exemplary embodiment.

Referring to FIG. 2, the adaptive bio-signal feature combining apparatus 200 includes a feature extractor 210, a stable interval determiner 220, a statistical variable calculator 230, and a feature combiner 240. The adaptive bio-signal feature combining apparatus 200 may be included in one or more processors.

The feature extractor 210 may extract first feature values and second feature values from a bio-signal. Here, the bio-signal may be an electrical signal transmitted between cells in vivo and may include an electrocardiogram (ECG) signal, a PPG signal, an electromyogram (EMG) signal, a ballistocardiogram (BCG) signal, etc.

According to one exemplary embodiment, a first feature may be a feature related to a cardiac output, and a second feature may be a feature related to the total peripheral vascular resistance.

According to an exemplary embodiment, a time interval may be divided into two intervals by the time corresponding to the third of numerous local maximum points included in a second-order differential bio-signal, and the time interval preceding the reference time may be determined as the systolic region and the subsequent time interval may be determined as the diastolic region.

The first and second features will be described later in detail with reference to FIGS. 3 to 5.

The stable interval determiner 220 may determine at least one stable interval in the bio-signal. Here, the stable interval may be an interval during which a blood pressure of an object is maintained stable and the bio-signal measured from the object remains stable.

According to an exemplary embodiment, the stable interval determiner 220 may determine at least one stable interval in the bio-signal using an output value of an acceleration or gyro sensor attached to the object. For example, the stable interval determiner 220 may compare the output value of the acceleration or gyro sensor at the time of bio-signal measurement with a predetermined threshold value, and, when the output value of the acceleration or gyro sensor is maintained less than or equal to the threshold value for a specified period of time, the stable interval determiner 220 may determine that the specified time period is a stable interval. When the output value of the acceleration or gyro sensor attached to the object exceeds the predetermined threshold value, the stable interval determiner 220 may determine that the object is in motion, and the blood pressure or the bio-signal of the object cannot be remain stable. By contrast, when the output value of the acceleration or gyro sensor attached to the object is maintained less than or equal to the predetermined threshold value for the specified period of time, the stable interval determiner 220 may determine that the object stays still or is in a stable state without a large movement, and may determine that the blood pressure or the bio-signal of the object is maintained stable. Therefore, the stable interval determiner 220 may be allowed to identify the stable interval of the bio-signal using the output value of the acceleration or gyro sensor attached to the object.

According to another exemplary embodiment, the stable interval determiner 220 may determine at least one stable interval in the bio-signal using the amount of change in the feature (e.g., the first feature or the second feature) extracted from the bio-signal. Here, the amount of change in the feature may mean the fluctuation with respect to the mean value of the corresponding feature. For example, the stable interval determiner 220 may calculate a variance, a standard deviation, and/or a mean absolute deviation of the feature values (e.g., first feature values or second feature values) extracted from a predetermined time interval of the bio-signal and calculate the amount of change in the feature by dividing the calculated variance, standard deviation, or mean absolute deviation by the mean of the feature values. The stable interval determiner 220 may compare the calculated amount of change in the feature with a predetermined threshold value and determine a corresponding time interval as a stable interval when the calculated amount of change in the feature is less than or equal to the predetermined threshold value.

The statistical variable calculator 230 may calculate statistical variable values of the first and second features for each stable interval based on the first feature values and the second feature values extracted from the stable intervals in the bio-signal. In this case, the statistical variable may include a mean, a variance, a standard deviation, a mean absolute deviation, and the like.

For example, the statistical variable calculator 230 may calculate the statistical variable values of the first and second features for each interval through Equation 2 and Equation 3.

$$x1_n = \frac{1}{M_n} \sum_{m=1}^{M_n} f1_n(m) \qquad (2)$$

$$x2_n = \frac{1}{M_n} \sum_{m=1}^{M_n} f2_n(m) \qquad (3)$$

Here, n denotes an index of a stable interval, $x1_n$ denotes a statistical variable value of the first feature of the n-th stable interval, $x2_n$ denotes a statistical variable value of the second feature of the n-th stable interval, $M_n$ denotes the total number of the first feature values or the second feature values that are extracted from the n-th stable interval, m denotes an index of the first feature value or the second feature value, $f1_n(m)$ denotes the m-th first feature value in the n-th stable interval, and $f2_n(m)$ denotes the m-th second feature value in the n-th stable interval.

In another example, the statistical variable calculator 230 may calculate the statistical variable values of the first and second features for each stable interval through Equation 4 and Equation 5.

$$x1_n = \frac{1}{M_n} \sum_{m=1}^{M_n} \left( f1_n(m) - \frac{1}{M_n} \sum_{m=1}^{M_n} f1_n(m) \right)^2 \qquad (4)$$

$$x2_n = \frac{1}{M_n} \sum_{m=1}^{M_n} \left( f2_n(m) - \frac{1}{M_n} \sum_{m=1}^{M_n} f2_n(m) \right)^2 \qquad (5)$$

Here, n denotes an index of a stable interval, $x1_n$ denotes a statistical variable value of the first feature of the n-th stable interval, $x2_n$ denotes a statistical variable value of the second feature of the n-th stable interval, $M_n$ denotes the total number of the first feature values or the second feature values that are extracted from the n-th stable interval, m denotes an index of the first feature value or the second feature value, $f1_n(m)$ denotes the m-th first feature value in the n-th stable interval, and $f2_n(m)$ denotes the m-th second feature value in the n-th stable interval.

In still another example, the statistical variable calculator 230 may calculate the statistical variable values of the first and second features for each stable interval through Equation 6 and Equation 7.

$$x1_n = \sqrt{\frac{1}{M_n} \sum_{m=1}^{M_n} \left( f1_n(m) - \frac{1}{M_n} \sum_{m=1}^{M_n} f1_n(m) \right)^2} \qquad (6)$$

$$x2_n = \sqrt{\frac{1}{M_n} \sum_{m=1}^{M_n} \left( f2_n(m) - \frac{1}{M_n} \sum_{m=1}^{M_n} f2_n(m) \right)^2} \qquad (7)$$

Here, n denotes an index of a stable interval, $x1_n$ denotes a statistical variable value of the first feature of the n-th stable interval, $x2_n$ denotes a statistical variable value of the second feature of the n-th stable interval, $M_n$ denotes the total number of the first feature values or the second feature values that are extracted from the n-th stable interval, m denotes an index of the first feature value or the second feature value, $f1_n(m)$ denotes the m-th first feature value in the n-th stable interval, and $f2_n(m)$ denotes the m-th second feature value in the n-th stable interval.

In still another example, the statistical variable calculator 230 may calculate the statistical variable values of the first and second features for each stable interval through Equation 8 and Equation 9.

$$x1_n = \frac{1}{M_n} \sum_{m=1}^{M_n} \left| f1_n(m) - \frac{1}{M_n} \sum_{m=1}^{M_n} f1_n(m) \right| \qquad (8)$$

$$x2_n = \frac{1}{M_n} \sum_{m=1}^{M_n} \left| f2_n(m) - \frac{1}{M_n} \sum_{m=1}^{M_n} f2_n(m) \right| \qquad (9)$$

Here, n denotes an index of a stable interval, $x1_n$ denotes a statistical variable value of the first feature of the n-th stable interval, $x2_n$ denotes a statistical variable value of the second feature of the n-th stable interval, $M_n$ denotes the total number of the first feature values or the second feature values that are extracted from the n-th stable interval, m denotes an index of the first feature value or the second feature value, $f1_n(m)$ denotes the m-th first feature value in the n-th stable interval, and $f2_n(m)$ denotes the m-th second feature value in the n-th stable interval.

The feature combiner 240 may combine the first feature and the second feature using the statistical variable values of the first feature and the second feature which are calculated for each stable interval.

According to one exemplary embodiment, the feature combiner 240 may calculate a combining coefficient for the first feature by averaging the statistical variable values of the first feature calculated for each stable interval and calculate a combining coefficient for the second feature by averaging the statistical variable values of the second feature calculated for each stable interval. In addition, the feature combiner 240 may combine the first feature and the second feature using the combining coefficient of the first feature and the combining coefficient of the second feature.

For example, the feature combiner 240 may combine the first feature and the second feature using Equation 10.

$$f_{comb} = \frac{1}{x1_{comb}} f1 + \frac{1}{x2_{comb}} f2, \text{ where} \quad (10)$$

$$x1_{comb} = \frac{1}{N} \sum_{n=1}^{N} x1_n, \, x2_{comb} = \frac{1}{N} \sum_{n=1}^{N} x2_n$$

Here, $f_{comb}$ denotes the combined feature, f1 denotes the first feature, f2 denotes the second feature, $x1_{comb}$ denotes the combining coefficient of the first feature, $x1_{comb}$ denotes the combining coefficient of the second feature, n denotes an index of the stable interval, $x1_n$ denotes a statistical variable value of the first feature in the n-th stable interval, and $x2_n$ denotes a statistical variable value of the second feature in the n-th stable interval.

In another example, the feature combiner 240 may combine the first feature and the second feature using Equation 11.

$$f_{comb} = u1 \left( \frac{1}{x1_{comb}} f1 + \frac{1}{x2_{comb}} f2 \right) + u2, \text{ where} \quad (11)$$

$$x1_{comb} = \frac{1}{N} \sum_{n=1}^{N} x1_n, \, x2_{comb} = \frac{1}{N} \sum_{n=1}^{N} x2_n$$

Here, $f_{comb}$ denotes the combined feature, f1 denotes the first feature, f2 denotes the second feature, $x1_{comb}$ denotes the combining coefficient of the first feature, $x1_{comb}$ denotes the combining coefficient of the second feature, n denotes an index of the stable interval, $x1_n$ denotes a statistical variable value of the first feature in the n-th stable interval, and $x2_n$ denotes a statistical variable value of the second feature in the n-th stable interval. In addition, u1 denotes a scaling coefficient, and u2 denotes a bias. u1 and u2 may be variously set according to the performance and purpose of the system.

In still another example, the feature combiner 240 may combine the first feature and the second feature using Equation 12.

$$f_{comb} = u1 \left( \frac{1}{x1_{comb}} f1 + a_{comb} \frac{1}{x2_{comb}} f2 \right) + u2, \text{ where} \quad (12)$$

$$x1_{comb} = \frac{1}{N} \sum_{n=1}^{N} x1_n, \, x2_{comb} = \frac{1}{N} \sum_{n=1}^{N} x2_n$$

Here, $f_{comb}$ denotes the combined feature, f1 denotes the first feature, f2 denotes the second feature, $x1_{comb}$ denotes the combining coefficient of the first feature, $x1_{comb}$ denotes the combining coefficient of the second feature, n denotes an index of the stable interval, $x1_n$ denotes a statistical variable value of the first feature in the n-th stable interval, and $x2_n$ denotes a statistical variable value of the second feature in the n-th stable interval. In addition, $a_{comb}$ is an amplification coefficient for $$\frac{1}{x2_{comb}},$$

which may be a setting factor given in the system in order to compensate for an imbalance which may occur in the degree of influence of $$\frac{1}{x1_{comb}} f1 \text{ versus } \frac{1}{x2_{comb}} f2 \text{ on } f_{comb}.$$

According to another exemplary embodiment, the feature combiner 240 may calculate a combining coefficient of each stable interval based on the statistical variable values of the first and second features which are calculated for each stable interval. For example, the feature combiner 240 may calculate the combining coefficient of each stable interval by dividing the statistical variable value of the first feature of each stable interval by the statistical variable value of the second feature of each stable interval. This is expressed as Equation 13.

$$w_n = \frac{x1_n}{x2_n} \quad (13)$$

Here, $W_n$ denotes a combining coefficient of the n-th stable interval, $x1_n$ denotes a statistical variable value of the first feature in the n-th stable interval, and $x2_n$ denotes a statistical variable value of the second feature in the n-th stable interval.

In addition, the feature combiner 240 may calculate an integrated combining coefficient by combining the combining coefficients calculated for each stable interval.

For example, the feature combiner 240 may calculate the integrated combining coefficient by arithmetically averaging the combining coefficients of the stable intervals. This is expressed as Equation 14.

$$w_{comb} = \frac{1}{N} \sum_{n=1}^{N} w_n \quad (14)$$

Here, $w_{comb}$ denotes an integrated combining coefficient, n denotes an index of a stable interval, and $W_n$ denotes a combining coefficient of the n-th stable interval.

In another example, the feature combiner 240 may calculate the integrated combining coefficient by applying different weights to the combining coefficients of the stable intervals and linearly combining the resulting combining coefficients. This is expressed as Equation 15.

$$w_{comb} = \sum_{n=1}^{N} \alpha_n w_n, \text{ where } \sum_{n=1}^{N} \alpha_n = 1 \quad (15)$$

Here, $w_{comb}$ denotes an integrated combining coefficient, n denotes an index of a stable interval, $W_n$ denotes a combining coefficient of the n-th stable interval, and $\alpha_n$ denotes a weight of the n-th stable interval. In this case, $\alpha_n$ may be set such that a higher weight is applied to a combining coefficient of a temporally later stable interval, which is, however, merely illustrative, and it is not limited thereto.

The feature combiner 240 may combine the first feature and the second feature based on the integrated combining coefficient. According to one exemplary embodiment, the feature combiner 240 may linearly combine the first and second features using the feature combining coefficient.

For example, the feature combiner 240 may combine the first and second features using Equation 16.

$$f_{comb} = f1 + w_{comb}f2 \quad (16)$$

Here, $f_{comb}$ denotes the combined feature, f1 denotes the first feature, f2 denotes the second feature, and $w_{comb}$ denotes the integrated combining coefficient.

In another example, the feature combiner 240 may combine the first and second features using Equation 17.

$$f_{comb} = u1(f1 + w_{comb}f2) + u2 \quad (17)$$

Here, $f_{comb}$ denotes the combined feature, f1 denotes the first feature, f2 denotes the second feature, $w_{comb}$ denotes the integrated combining coefficient, u1 denotes a scaling coefficient, and u2 denotes a bias. Here, u1 and u2 may be set variously according to the performance and purpose of the system.

In still another example, the feature combiner 240 may combine the first and second features using Equation 18.

$$f_{comb} = u1(f1 + a_{comb}w_{comb}f2) + u2 \quad (18)$$

Here, $f_{comb}$ denotes the combined feature, f1 denotes the first feature, f2 denotes the second feature, $w_{comb}$ denotes the integrated combining coefficient, u1 denotes a scaling coefficient, and u2 denotes a bias. $a_{comb}$ is an amplification coefficient for the $w_{comb}$, which is a setting factor given in the system in order to compensate for an imbalance which may occur in the degree of influence of $w_{comb}*f2$ versus f1 on $f_{comb}$.

Figure 3:
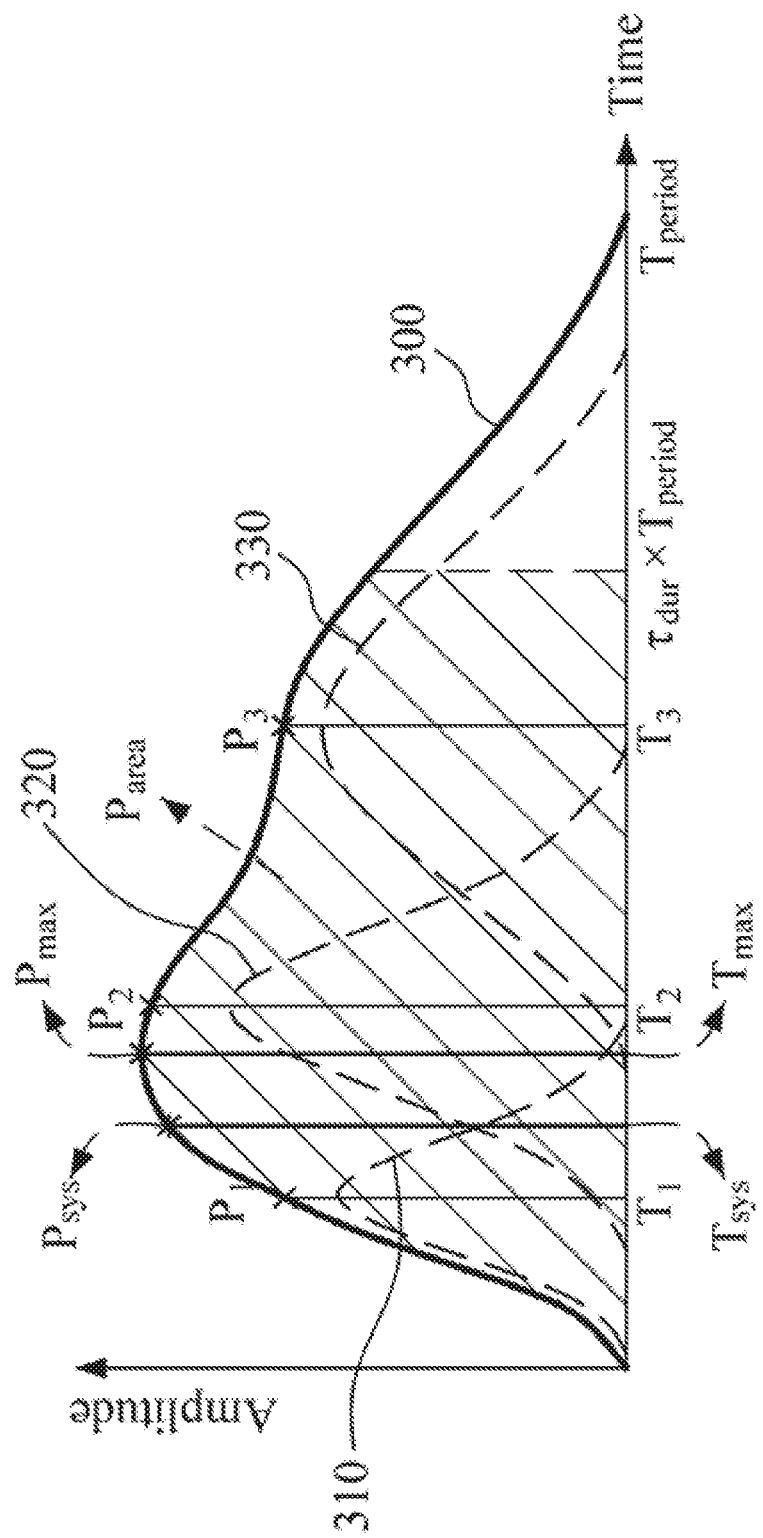
FIG. 3 is a graph for describing a first feature and a second feature of a bio-signal.
Figure 4:
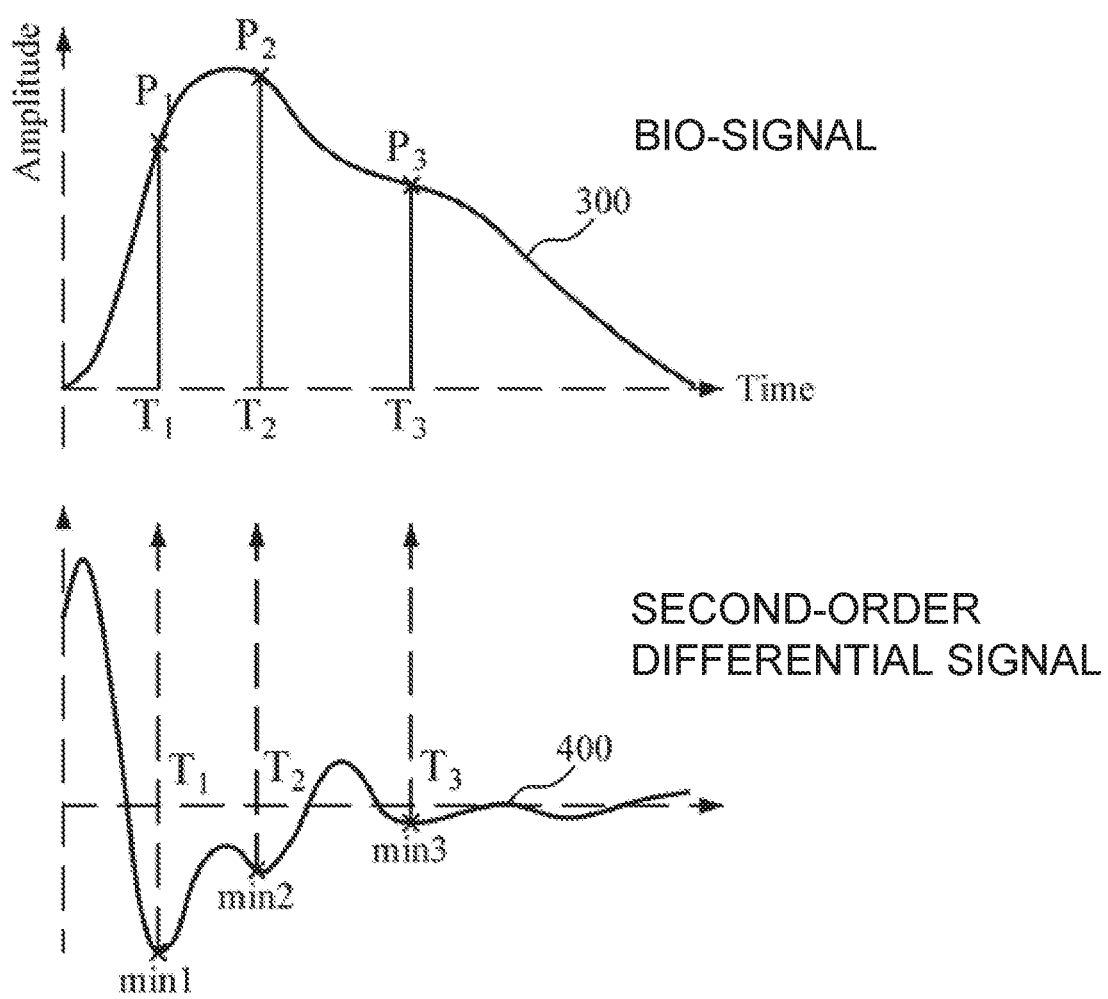
FIG. 4 illustrates graphs for describing a method of obtaining $P_n(P_1, P_2, P_3)$ and $T_n(T_1, T_2, T_3)$ of FIG. 3.
Figure 5:
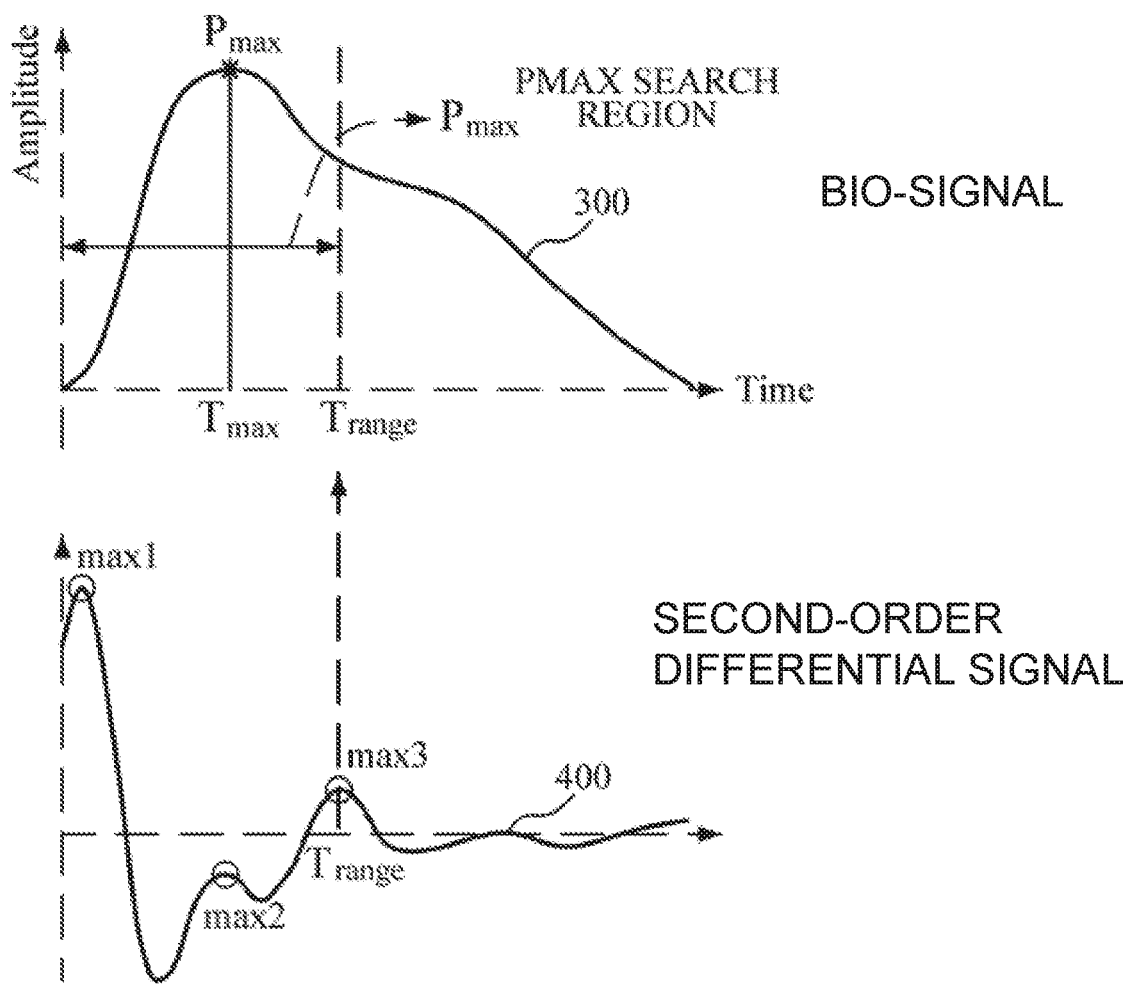
FIG. 5 illustrates graphs for describing a method of obtaining $P_{max}$ and $T_{max}$ of FIG. 3.

FIG. 3 is a graph for describing a first feature and a second feature of a bio-signal, FIG. 4 illustrates graphs for describing a method of obtaining $P_n(P_1, P_2, P_3)$ and $T_n(T_1, T_2, T_3)$ of FIG. 3, and FIG. 5 illustrates graphs for describing a method of obtaining $P_{max}$ and $T_{max}$ of FIG. 3.

Referring to FIG. 3, the bio-signal 300 may be a superposition of three component pulses 310, 320, and 330. In this case, reference numeral 300 denotes the bio-signal of one period $T_{period}$, 320 denotes a second component pulse, and 330 denotes a third component pulse. In addition, $T_1$ denotes the time of the peak point of the first component pulse 310, $P_1$ denotes the amplitude of the bio-signal 300 at $T_1$, $T_2$ denotes the time of the peak point of the second component pulse 320, $P_2$ denotes the amplitude of the bio-signal 300 at $T_2$, $T_3$ denotes the time of the peak point of the third component pulse 330, $P_3$ denotes the amplitude of the bio-signal 300 at $T_3$, $T_{max}$ denotes the time of the peak point of the bio-signal 300 in a predetermined interval (e.g., a first interval), $P_{max}$ denotes the amplitude of the bio-signal 300 at $T_{max}$, $T_{sys}$ denotes the intermediate time between $T_1$ and $T_{max}$, $P_{sys}$ denotes the amplitude of the bio-signal 300 at $T_{sys}$, $\tau_{dur}$ denotes a setting factor ($0 \leq \tau_{dur} \leq 1$) (e.g., 0.7) of the system, and $P_{area}$ denotes the sum of amplitudes of the bio-signal 300 between time 0 and $\tau_{dur}*T_{period}$ (in a second interval).

The first feature is a feature related to the cardiac output, and it may include, for example, $P_{max}/P_{area}$, $P_{max}/P_3$, $P_{sys}/P_3$, $P_1/P_3$, $P_2/P_3$, $1/T_{period}$, or the like.

The second feature is a feature related to the total peripheral vascular resistance, and it may include $1/(T_3-T_{sys})$, $1/(T_3-T_{max})$, $1/(T_3-T_1)$, $1/(T_3-T_2)$, $P_3/P_1$, $P_2/P_1$, or the like.

Meanwhile, $T_{sys}$ is described as the intermediate time between $T_1$ and $T_{max}$ in FIG. 3, but is not limited thereto. For example, $T_{sys}$ may be an arbitrary internally dividing point between $T_1$ and $T_{max}$ or an arbitrary internally dividing point between $T_1$ and $T_2$.

Referring to FIG. 4, $P_n(P_1, P_2, P_3)$ and $T_n(T_1, T_2, T_3)$ of FIG. 3 may be obtained based on a second-order differential signal 400 of the bio-signal 300. When the second-order differential signal 400 is obtained from the bio-signal 300, the second-order differential signal 400 may include a plurality of local minimum points $\min_1$, $\min_2$, and $\min_3$. When the local minimum points $m_1$ to $m_3$ included in the second-order differential signal 400 are arranged in a time-order sequence, the local minimum point $m_1$ corresponds to $T_1$, the second local minimum point $m_2$ corresponds to $T_2$, and the third local minimum point $m_3$ corresponds to $T_3$. In addition, the amplitude of the bio-signal 300 at $T_1$ corresponds to $P_1$, the amplitude of the bio-signal 300 at $T_2$ corresponds to $P_2$, and the amplitude of the bio-signal 300 at $T_3$ corresponds to $P_3$.

Referring to FIG. 5, $P_{max}$ and $T_{max}$ of FIG. 3 may be obtained based on the second-order differential signal 400 of the bio-signal 300. When the second-order differential signal 400 is obtained from the bio-signal 300, the second-order differential signal 400 may include a plurality of local maximum points $\max_1$, $\max_2$, and $\max_3$. When the local maximum points $\max_1$ to $\max_3$ included in the second-order differential signal 400 are arranged in a time-order sequence and the time corresponding to the third maximum point is $T_{range}$, a range for searching $P_{max}$ may be determined to be the range of $0 \leq time \leq T_{range}$ In this case, the time of the peak point of the bio-signal 300 in the range of $0 \leq time \leq T_{range}$ corresponds to $T_{max}$ and the amplitude of the bio-signal 300 at $T_{max}$ corresponds to $P_{max}$.

Figure 6:
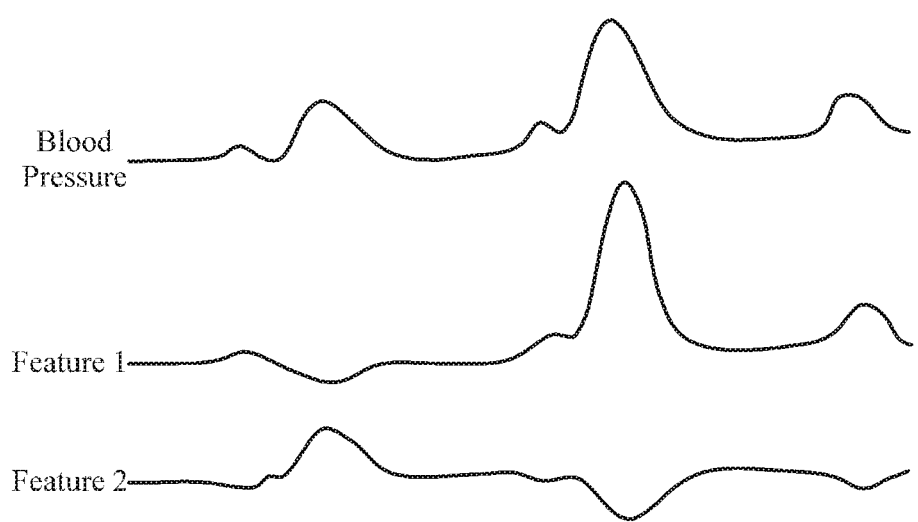
FIG. 6 is a diagram showing an example of change of a blood pressure and changes of the first feature and the second feature extracted from the bio-signal.

FIG. 6 is a diagram showing an example of change of a blood pressure and changes of the first feature and the second feature extracted from the bio-signal.

Referring to FIG. 6, when a blood pressure value changes, the average change value of the first feature (denoted as FEATURE 1) and the average change value of the second feature (denoted as FEATURE 2) may also change. Specifically, when the cardiac output increases due to exercise or the like and the blood pressure, in turn, rises, the first feature (FEATURE 1) related to the cardiac output, may increase greatly, whereas the second feature (FEATURE 2) related to the total peripheral vascular resistance, may be substantially constant or decreases. In addition, when the blood vessel resistance increases due to the tension of tissue and in turn the blood pressure increases, the second feature (FEATURE 2) related to the total peripheral vascular resistance may increase greatly, whereas the first feature (FEATURE 1) related to the cardiac output may be substantially constant or decreases. In other words, when the blood pressure is out of the stable state, i.e., a stable interval, the balance between changes of the two features is generally disturbed and the change of one feature is relatively larger than the other feature, which may result in change in blood pressure.

Figure 7A:
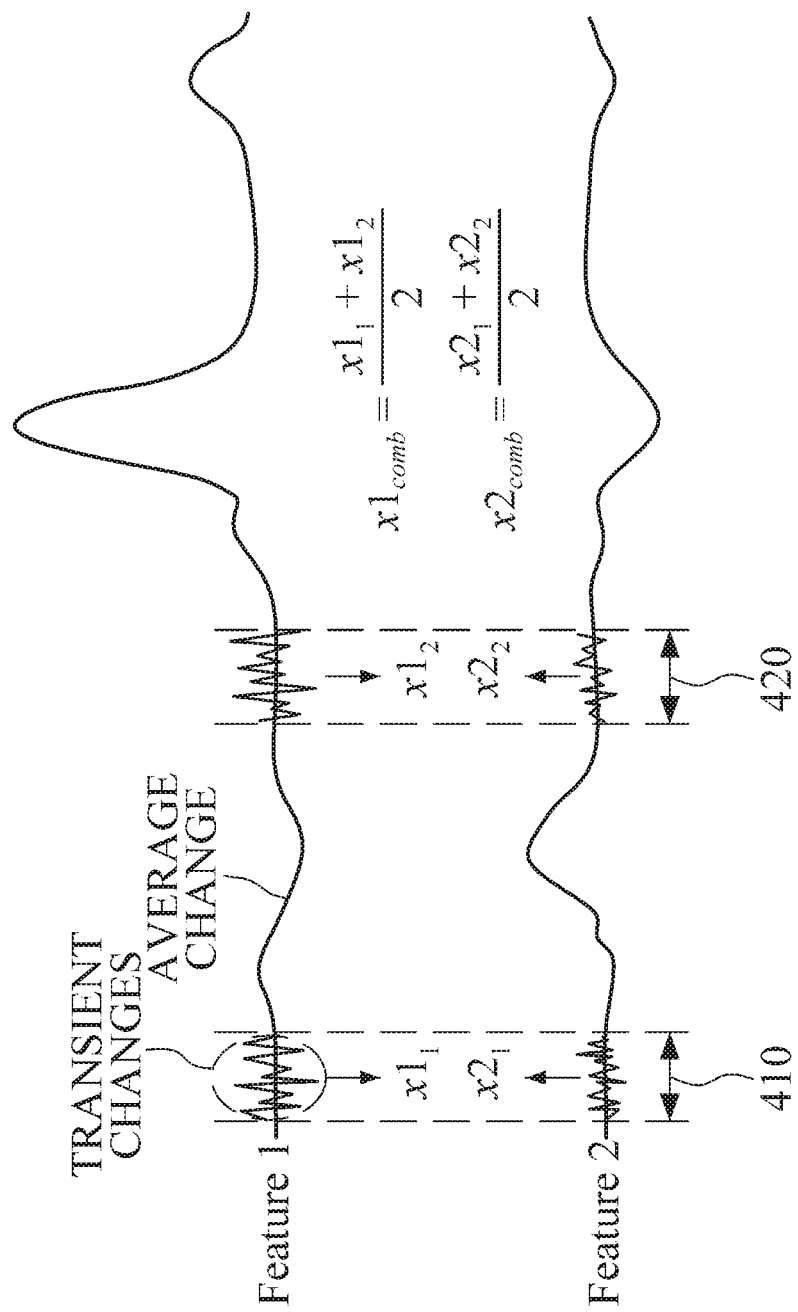
FIG. 7A is a diagram for describing the process of obtaining a combining coefficient of each feature.

FIG. 7A is a diagram for describing the process of obtaining a combining coefficient of each feature. Specifically, FIG. 7A is a diagram for describing the process of obtaining the combining coefficients of the first feature and the second feature based on the first feature values and the second feature values which are extracted from two stable intervals.

Referring to FIGS. 2 and 7A, the feature extractor 210 may extract the first feature values and the second feature values from the bio-signal, and the stable interval determiner 220 may determine the two stable intervals 410 and 420 from the bio-signal.

The statistical variable calculator 230 may calculate a statistical variable value $x1_1$ of the first feature based on the first feature values in a first stable interval 410 and calculate a statistical variable $x2_1$ of the second feature based on the second feature values in the first stable interval 410. In addition, the statistical variable calculator 230 may calculate a statistical variable value $x1_2$ of the first feature based on the first feature values in a second stable interval 420 and calculate a statistical variable value $x2_2$ of the second feature based on the second feature values in the second stable interval 420. In this case, the statistical variable calculator 230 may calculate the statistical variable values $x1_1$ and $x1_2$ of the first feature and the statistical variable values $x2_1$ and $x2_2$ of the second feature using Equation 2 to Equation 9.

The feature combiner 240 may calculate a combining coefficient $x1_{comb}$ of the first feature by arithmetically averaging the statistical variable values $x1_1$ and $x1_2$ of the first feature and calculate a combining coefficient $x2_{comb}$ of the second feature by arithmetically averaging the statistical variable values $x2_1$ and $x2_2$ of the second feature.

Meanwhile, the feature combiner 240 may combine the first feature and the second feature using Equation 10 to Equation 12, based on the combining coefficient $x1_{comb}$ of the first feature and the combining coefficient $x2_{comb}$ of the second feature.

FIG. 7B is a diagram for describing the process of obtaining an integrated combining coefficient. Specifically, FIG. 7B is a diagram for describing the process of obtaining the integrated combining coefficient based on the first feature values and the second feature values which are extracted from two stable intervals.

Referring to FIGS. 2 and 7B, the feature extractor 210 may extract the first feature values and the second feature values from the bio-signal, and the stable interval determiner 220 determines the two stable intervals 410 and 420 from the bio-signal.

The statistical variable calculator 230 may calculate a statistical variable $x1_1$ of the first feature based on the first feature values in a first stable interval 410 and calculates a statistical variable $x2_1$ of the second feature based on the second feature values in the first stable interval 410. In addition, the statistical variable calculator 230 may calculate a statistical variable value $x1_2$ of the first feature based on the first feature values in a second stable interval 420 and calculates a statistical variable value $x2_2$ of the second feature based on the second feature values in the second stable interval 420. In this case, the statistical variable calculator 230 may calculate the statistical variable value $x1_1$ and $x1_2$ of the first feature and the statistical variable value $x2_1$ and $x2_2$ of the second feature using Equation 2 to Equation 9.

The feature combiner 240 may calculate a combining coefficient $w_1$ of the first stable interval 410 based on the statistical variable values $x1_1$ and $x2_1$ of the first and second features. In addition, the feature combiner 240 calculates a combining coefficient $w_2$ of the second stable interval 420 based on the statistical variable values $x1_2$ and $x2_2$ of the first and second features. In this case, the feature combiner 240 may calculate the combining coefficient $w_1$ of the first stable interval 410 and the combining coefficient $w_2$ of the second stable interval 420 using Equation 13.

The feature combiner 240 may calculate an integrated combining coefficient $w_{comb}$ by arithmetically averaging the combining coefficients $w_1$ and $w_2$ of the stable intervals.

Meanwhile, the feature combiner 240 may combine the first feature and the second feature using Equation 16 to Equation 18 based on the integrated combining coefficient $w_{comb}$.

Figure 8:
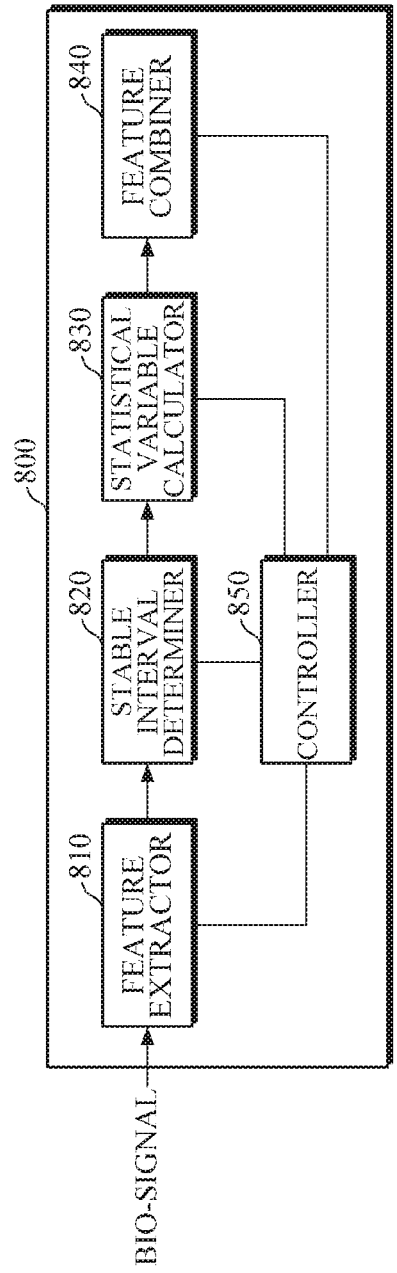
FIG. 8 is a block diagram is a block diagram illustrating an adaptive bio-signal feature combining apparatus according to another exemplary embodiment.
Figure 9:
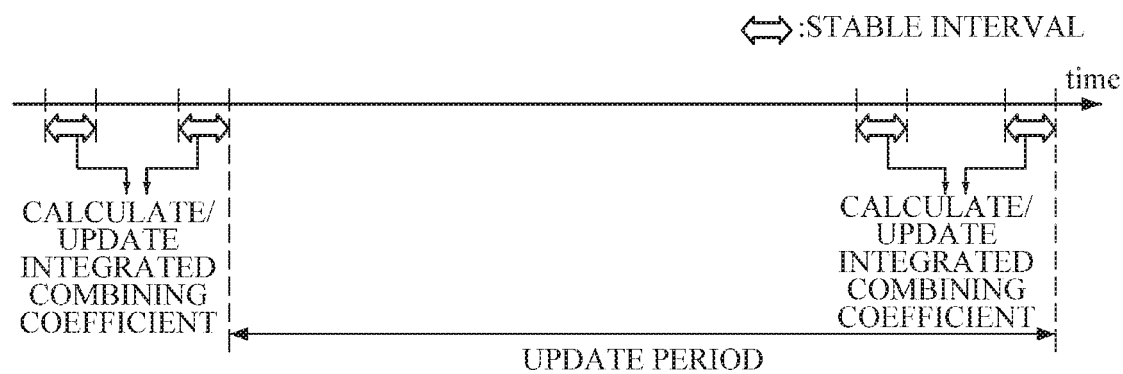
FIG. 9 is a diagram illustrating an example of periodically updating an integrated combining coefficient.
Figure 10:
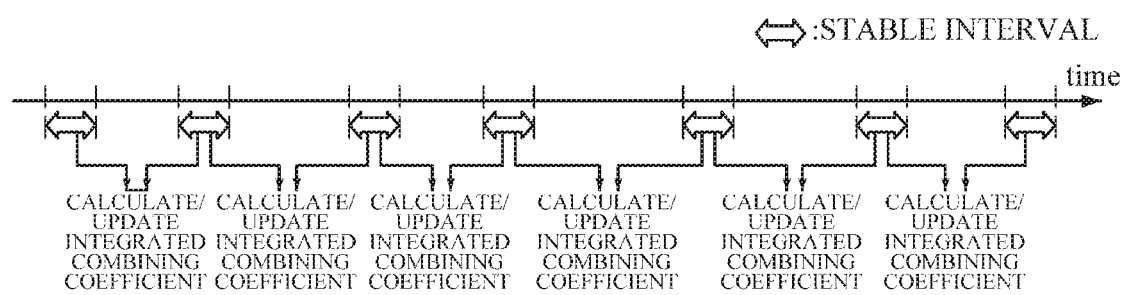
FIG. 10 is a diagram illustrating an example of updating an integrated combining coefficient in a sliding-window scheme.

FIG. 8 is a block diagram is a block diagram illustrating an adaptive bio-signal feature combining apparatus according to another exemplary embodiment, FIG. 9 is a diagram illustrating an example of periodically updating an integrated combining coefficient, and FIG. 10 is a diagram illustrating an example of updating an integrated combining coefficient in a sliding-window scheme.

Referring to FIGS. 8 to 10, the adaptive bio-signal feature combining apparatus 800 includes a feature extractor 810, a stable interval determiner 820, a statistical variable calculator 830, a feature combiner 840, and a controller 850. The feature extractor 810, the stable interval determiner 820, the statistical variable calculator 830, the feature combiner 840, and the controller 850 may be included in one or more processors. In this case, the feature extractor 810, the stable interval determiner 820, the statistical variable calculator 830, and the feature combiner 840 may operate in substantially the same manner as the feature extractor 210, the stable interval determiner 220, the statistical variable calculator 230, and the feature combiner 240 of FIG. 2, respectively, and thus detailed descriptions thereof will not be reiterated.

The controller 850 may constantly update a feature combining coefficient of a first feature and a combining coefficient of a second feature, or may constantly update an integrated combining coefficient.

The features of the bio-signal may change according to changes in physiological characteristics of the human body and changes in the surrounding environment (e.g., temperature, etc.). Accordingly, the controller 850 may control the feature extractor 810, the stable interval determiner 820, the statistical variable calculator 830, and the feature combiner 840 so that the combining coefficients of the first feature and the second feature can be constantly updated or the feature combining coefficient can be constantly updated by taking into account the features of the bio-signal.

According to one exemplary embodiment, the controller 850 may control the feature extractor 810, the stable interval determiner 820, the statistical variable calculator 830, and the feature combiner 840 to periodically update the integrated combining coefficient according to a designated update period, as shown in FIG. 9. In this case, the update period may be set variously according to the performance or purpose of the system.

According to another exemplary embodiment, the controller 850 may control the feature extractor 810, the stable interval determiner 820, the statistical variable calculator 830, and the feature combiner 840 so that the integrated combining coefficient can be constantly updated by overlapping at least one stable interval in a sliding-window scheme, as shown in FIG. 10.

Meanwhile, although FIGS. 9 and 10 illustrate that the integrated combining coefficient is constantly updated for convenience of description, it is possible to constantly update the combining coefficients of the first and second features according to an exemplary embodiment.

Figure 11:
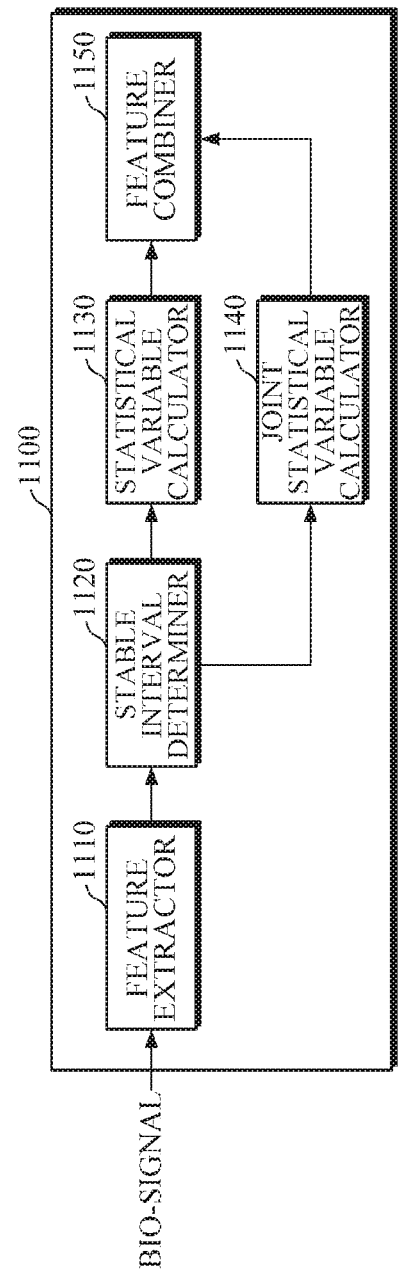
FIG. 11 is a block diagram illustrating an adaptive bio-signal feature combining apparatus according to another exemplary embodiment.

FIG. 11 is a block diagram illustrating an adaptive bio-signal feature combining apparatus according to another exemplary embodiment.

Referring to FIG. 11, the adaptive bio-signal feature combining apparatus 1100 may include a feature extractor 1110, a stable interval determiner 1120, a statistical variable calculator 1130, a joint statistical variable calculator 1140, and a feature combiner 1150. Here, the feature extractor 1110, the stable interval determiner 1120, and the statistical variable calculator 1130 may operate in substantially the same manner as the feature extractor 210, the stable interval determiner 220, and the statistical variable calculator 230 of FIG. 2, respectively, and thus detailed descriptions thereof will not be reiterated.

The joint statistical variable calculator 1140 may calculate a joint statistical variable value between a first feature and a second feature. In this case, the joint statistical variable may include a covariance or a correlation coefficient, which is, however, merely illustrative, and it is not limited thereto.

As described above, since the change in blood pressure is minimized in an interval in which a user remains stable by having a rest or the like, that is, a stable interval, a result of combination of the first and second features extracted from the bio-signal in the stable interval may be expected to have a small fluctuation. Therefore, the combining coefficient may be adjusted such that a variance that indicates statistical fluctuation of a sum of f1 and wf2, which is the combination result of the two features, is minimized. This may be expressed as Equation 19.

$$V[f1 + wf2] = E[(f1 + wf2)^2] - (E[f1 + wf2])^2 \quad (19)$$
$$= E[f1^2 + 2wf1f2 + w^2f1^2] - E[f1]^2 -$$
$$2wE[f1]E[f2] - w^2(E[f2])^2$$
$$= w^2V[f2] + 2w(E[f1f2] - E[f1]E[f2]) + V[f1]$$

Here, V[X] and E[X] denote a variance and a mean of variable X, respectively, f1 denotes a first feature, f2 denotes a second feature, and w denotes an integrated combining coefficient.

Referring to Equation 19, it is shown that w that minimizes V[f1+wf2] is obtained as Equation 20.

$$w = -\frac{E[f1f2] - E[f1]E[f2]}{V[f2]} = -\frac{COV(f1, f2)}{V[f2]} \quad (20)$$

Here, COV(f1, f2) is a covariance between f1 and f2.

Referring to Equation 15, it is shown that the combining coefficient w can be obtained using the statistical variable (variance) v[f2] of the second feature and the covariance COV(f1, f2) between the first feature and the second feature.

Equation 20 is expanded as shown in Equation 21.

$$w = -\frac{x1x2}{V[f2]} \times \frac{COV(f1, f2)}{x1x2} = -\frac{x1}{x2} \times \rho_{f1,f2} \quad (21)$$

Here, x1 and x2 denote a statistical variable of the first feature and a statistical variable of the second feature, respectively, $\rho_{f1,f2}$ denotes the correlation coefficient between the first feature and the second feature.

Figure 21:
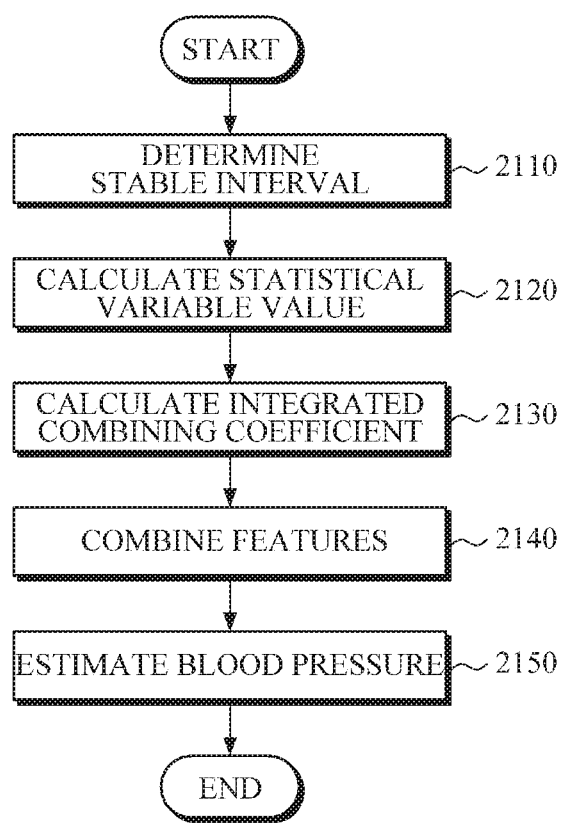
FIG. 21 is a flowchart illustrating a blood pressure measurement method according to an exemplary embodiment.

Referring to FIG. 21, it is shown that the combining coefficient w is obtained using the statistical variable x1 of the first feature, the statistical variable x2 of the second feature, and the correlation coefficient $\rho_{f1,f2}$ between the first feature and the second feature.

The feature combiner 1150 may calculate the combining coefficient of each stable interval based on the statistical variable of the first feature, the statistical variable of the second feature, and the joint statistical variable (e.g., a covariance, a correlation coefficient, or the like) between the first feature and the second feature. For example, the feature combiner 1150 may calculate the combining coefficient of each stable interval using Equation 20 or Equation 21.

The feature combiner 1150 may calculate the integrated combining coefficient by combining the combining coefficients calculated for each stable interval. For example, the feature combiner 1150 may calculate the integrated combining coefficient using Equation 14 or Equation 15.

The feature combiner 1150 may generate a combined feature by combining the first feature and the second feature based on the integrated combining coefficient. For example, the feature combiner 1150 may combine the first and second features using Equation 16 to Equation 18.

Figure 12:
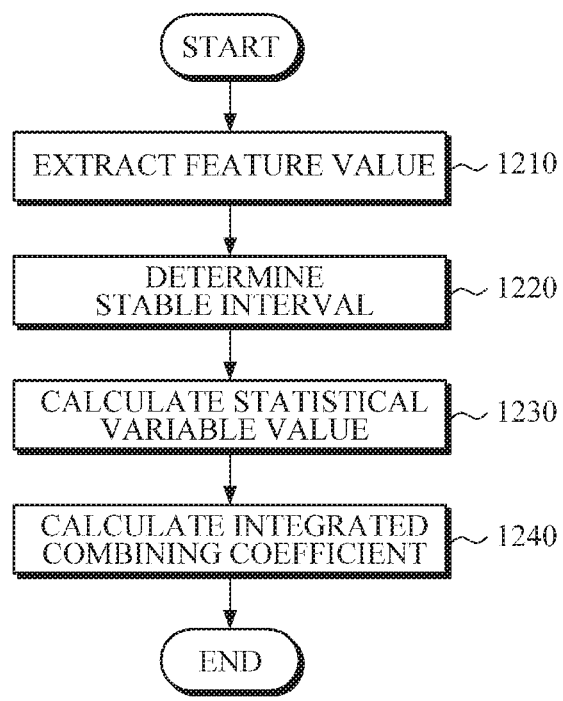
FIG. 12 is a flowchart illustrating an adaptive bio-signal feature combining method according to an exemplary embodiment.

FIG. 12 is a flowchart illustrating an adaptive bio-signal feature combining method according to an exemplary embodiment. The adaptive bio-signal feature combining method of FIG. 12 may be performed by the adaptive bio-signal feature combining apparatus 200 of FIG. 2.

Referring to FIGS. 2 and 12, the adaptive bio-signal feature combining apparatus 200 extracts first feature values and second feature values are extracted from a bio-signal of an object, in operation 1210. Here, the first feature and the second feature have been described specifically with reference to FIGS. 2 to 5, and hence detailed descriptions thereof will be omitted.

The adaptive bio-signal feature combining apparatus 200 determines at least one stable interval in the bio-signal, as depicted in operation 1220.

According to one exemplary embodiment, the adaptive bio-signal feature combining apparatus 200 may determine at least one stable interval in the bio-signal using an acceleration sensor or a gyro sensor which is attached to an object. In a case where the adaptive bio-signal feature combining apparatus 200 and the acceleration or gyro sensor are included in a smartwatch or a smartphone, the acceleration or gyro sensor may detect the motion of a user who is wearing the smartwatch or holding the smartphone, and the adaptive bio-signal feature combining apparatus 200 may determine the stable interval based on the detected motion. For example, the adaptive bio-signal feature combining apparatus 200 may compare an output value of the acceleration sensor or the gyro sensor with a predetermined threshold value, and, when the output value of the acceleration or gyro sensor is maintained less than or equal to the threshold value for a specified period of time, the adaptive bio-signal feature combining apparatus 200 may determine that the specified time period is a stable interval.

According to another exemplary embodiment, the adaptive bio-signal feature combining apparatus 200 may determine at least one stable interval in the bio-signal using the amount of change in the feature (e.g., the first feature or the second feature) extracted from the bio-signal. Here, the amount of change in the feature may mean the fluctuation with respect to the mean value of the corresponding feature. For example, the adaptive bio-signal feature combining apparatus 200 may calculate a variance, a standard deviation, a mean absolute deviation, etc. of the feature values (e.g., first feature values or second feature values) extracted from a predetermined time interval of the bio-signal and calculate the amount of change in the feature by dividing the calculated variance, standard deviation, or mean absolute deviation by the mean of the feature values. The adaptive bio-signal feature combining apparatus 200 may compare the calculated amount of change in the feature with a predetermined threshold value and determine the corresponding time interval as a stable interval when the calculated amount of change in the feature is less than or equal to the predetermined threshold value.

The adaptive bio-signal feature combining apparatus 200 calculates a statistical variable value of the first feature and a statistical variable value of the second feature for each stable interval based on the first feature values and the second feature values, in operation 1230. In this case, the statistical variable may include a mean, a variance, a standard deviation, a mean absolute deviation, and the like. For example, the adaptive bio-signal feature combining apparatus 200 may calculate the statistical variable values of the first and second features using Equation 2 to Equation 9.

The adaptive bio-signal feature combining apparatus 200 calculates an integrated combining coefficient based on the statistical variable values of the first and second features which are calculated for each stable interval, in operation 1240.

Hereinafter, operation 1240 in which the integrated combining coefficient is calculated will be described in detail with reference to FIG. 13.

Figure 13:
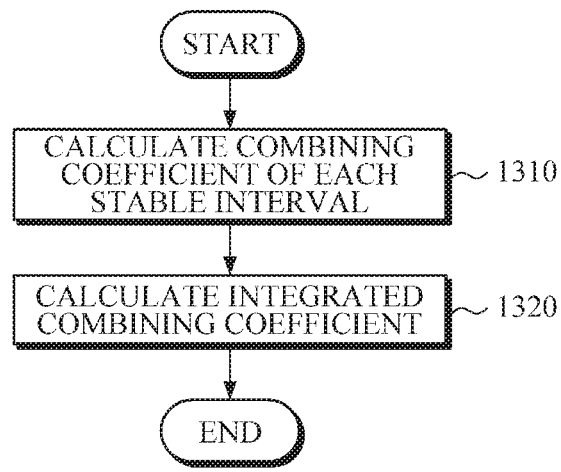
FIG. 13 is a flowchart illustrating operation in which the feature combining coefficient is calculated according to an exemplary embodiment.

FIG. 13 is a flowchart illustrating operation in which the integrated combining coefficient is calculated, according to an exemplary embodiment.

Referring to FIGS. 2 and 13, the adaptive bio-signal feature combining apparatus 200 calculates the combining coefficient of each stable interval based on the statistical variable values of the first and second features which are calculated for each stable interval, in operation 1310. For example, the adaptive bio-signal feature combining apparatus 200 may calculate the combining coefficient of each stable interval using Equation 13.

The adaptive bio-signal feature combining apparatus 200 calculates the integrated combining coefficient by combining the combining coefficients calculated for each stable interval, in operation 1320. For example, the adaptive bio-signal feature combining apparatus 200 may calculate the integrated combining coefficient using Equation 14 or Equation 15.

Figure 14:
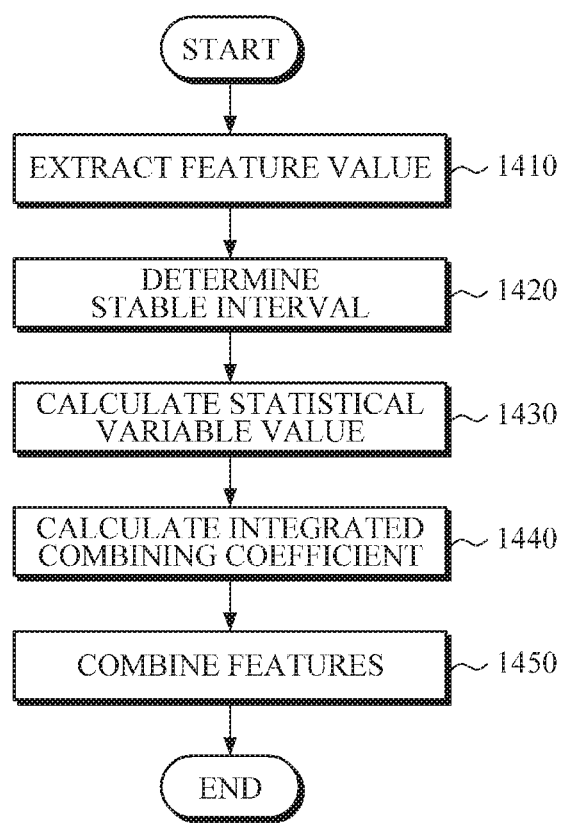
FIG. 14 is a flowchart illustrating an adaptive bio-signal feature combining method according to another exemplary embodiment.

FIG. 14 is a flowchart illustrating an adaptive bio-signal feature combining method according to another exemplary embodiment. The adaptive bio-signal feature combining method of FIG. 14 may be performed by the adaptive bio-signal feature combining apparatus 200 of FIG. 2. Here, operations 1410 to 1440 may be substantially the same as operations 1210 to 1240 of FIG. 12, and thus detailed descriptions thereof will be omitted.

In operation 1450, the adaptive bio-signal feature combining apparatus 200 combines the first feature and the second feature based on the integrated combining coefficient. For example, the adaptive bio-signal feature combining apparatus 200 may combine the first feature and the second feature using Equation 16 to Equation 18.

Figure 15:
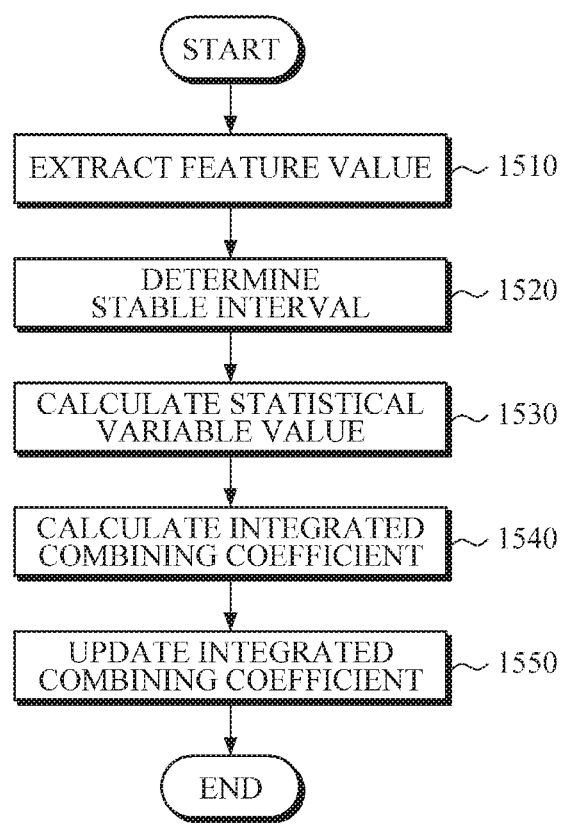
FIG. 15 is a flowchart illustrating an adaptive bio-signal feature combining method according to another exemplary embodiment.

FIG. 15 is a flowchart illustrating an adaptive bio-signal feature combining method according to another exemplary embodiment. The adaptive bio-signal feature combining method of FIG. 15 may be performed by the adaptive bio-signal feature combining apparatus 800 of FIG. 8. Here, operations 1510 to 1540 may be substantially the same as operations 1210 to 1240 of FIG. 12, and thus detailed descriptions thereof will be omitted.

In 1550, the adaptive bio-signal feature combining apparatus 800 constantly updates the integrated combining coefficient.

According to one embodiment, the adaptive bio-signal feature combining apparatus 800 may repeatedly perform operations 1510 to 1540 so as to periodically update the integrated combining coefficient according to a designated update period, as shown in FIG. 9.

According to another exemplary embodiment, the adaptive bio-signal feature combining apparatus 800 may repeatedly perform operations 1510 to 1540 to constantly update the integrated combining coefficient by overlapping at least one stable interval in a sliding-window scheme, as shown in FIG. 10.

Figure 16:
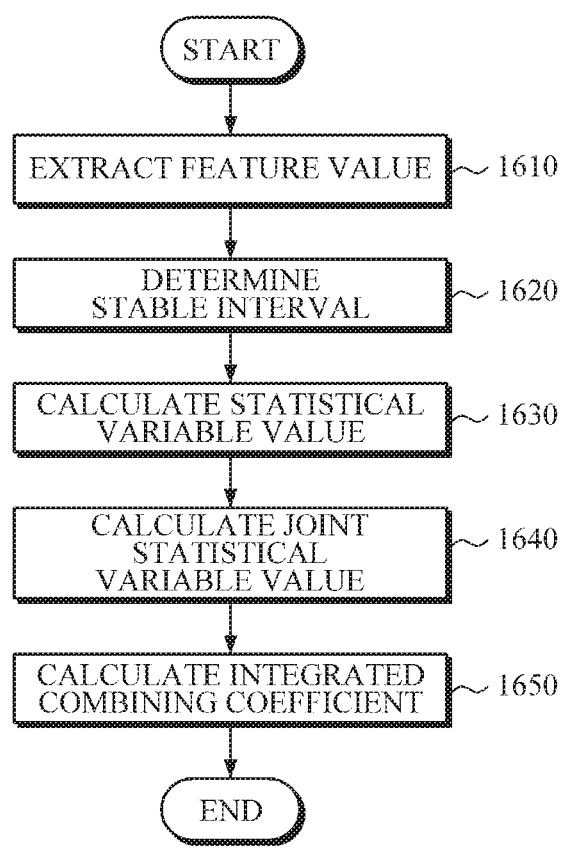
FIG. 16 is a flowchart illustrating an adaptive bio-signal feature combining method according to another exemplary embodiment.

FIG. 16 is a flowchart illustrating an adaptive bio-signal feature combining method according to another exemplary embodiment. The adaptive bio-signal feature combining method of FIG. 16 may be performed by the adaptive bio-signal feature combining apparatus 1100 of FIG. 11. Here, operations 1610 to 1630 may be substantially the same as operations 1210 to 1230 of FIG. 12, and thus detailed descriptions thereof will be omitted.

In operation 1640, the adaptive bio-signal feature combining apparatus 1100 calculates a joint statistical variable value between the first feature and the second feature. In particular, the joint statistical variable may include a covariance or a correlation coefficient, which is, however, merely illustrative, and it is not limited thereto.

In operation 1650, the adaptive bio-signal feature combining apparatus 1100 calculates the combining coefficient of each stable interval based on the statistical variable of the first feature, the statistical variable of the second feature, and the joint statistical variable between the first feature and the second feature, and calculates the feature combining coefficient by combining the combining coefficients calculated for each stable interval. For example, the adaptive bio-signal feature combining apparatus 1100 may calculate the combining coefficient of each stable interval using Equation 20 or Equation 21, and calculates the integrated combining coefficient using Equation 14 or Equation 15.

Figure 17:
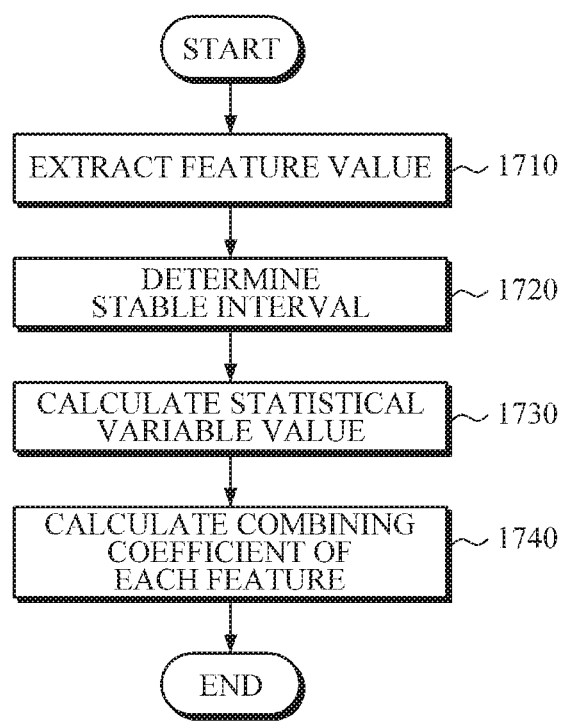
FIG. 17 is a flowchart illustrating an adaptive bio-signal feature combining method according to another exemplary embodiment.

FIG. 17 is a flowchart illustrating an adaptive bio-signal feature combining method according to another exemplary embodiment. The adaptive bio-signal feature combining method of FIG. 17 may be performed by the adaptive bio-signal feature combining apparatus 200 of FIG. 2. Here, operations 1710 to 1730 may be substantially the same as operations 1210 to 1230 of FIG. 12, and thus detailed descriptions thereof will be omitted.

In operation 1740, the adaptive bio-signal feature combining apparatus 200 calculates a combining coefficient of the first feature by averaging statistical variable values of the first feature calculated for each stable interval, and calculates a combining coefficient of the second feature by averaging statistical variable values of the second feature calculated for each stable interval.

Figure 18:
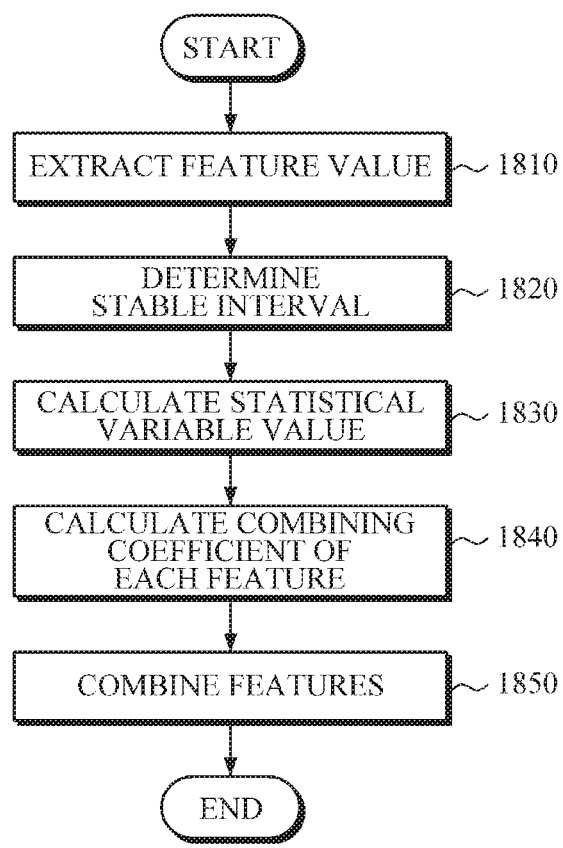
FIG. 18 is a flowchart illustrating an adaptive bio-signal feature combining method according to still another exemplary embodiment.

FIG. 18 is a flowchart illustrating an adaptive bio-signal feature combining method according to still another exemplary embodiment. The adaptive bio-signal feature combining method of FIG. 18 may be performed by the adaptive bio-signal feature combining apparatus 200 of FIG. 2. Here, operations 1810 to 1840 may be substantially the same as operations 1710 to 1740 of FIG. 17, and thus detailed descriptions thereof will be omitted.

In operation 1850, the adaptive bio-signal feature combining apparatus 200 combines a first feature and a second feature based on combining coefficients of the respective features. For example, the adaptive bio-signal feature combining apparatus 200 may combine the first feature and the second feature using Equation 10 to Equation 12.

Figure 19:
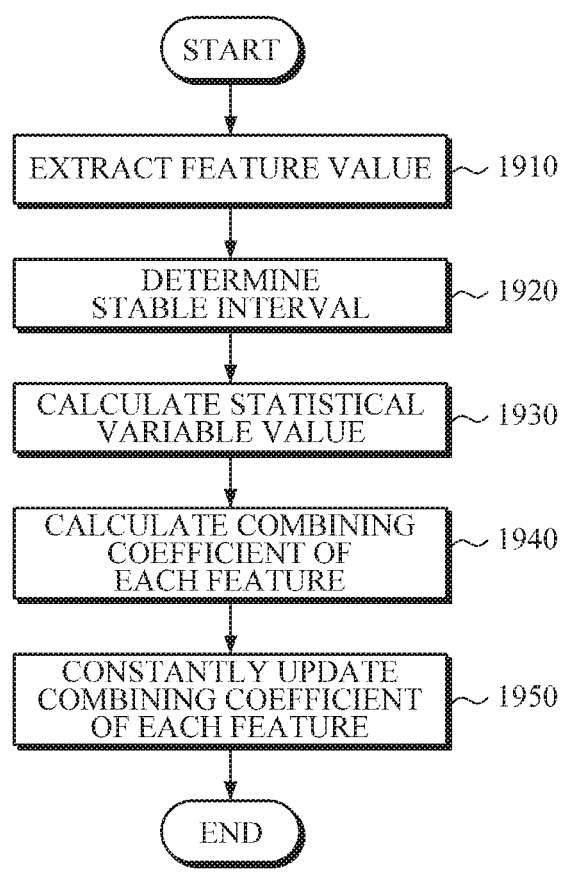
FIG. 19 is a flowchart illustrating an adaptive bio-signal feature combining method according to yet another exemplary embodiment.

FIG. 19 is a flowchart illustrating an adaptive bio-signal feature combining method according to yet another exemplary embodiment. The adaptive bio-signal feature combining method of FIG. 19 may be performed by the adaptive bio-signal feature combining apparatus 800 of FIG. 8. Here, operations 1910 to 1940 may be substantially the same as operations 1710 to 1740 of FIG. 17, and thus detailed descriptions thereof will be omitted.

In operation 1950, the adaptive bio-signal feature combining apparatus 800 constantly updates combining coefficients of each of features.

According to one exemplary embodiment, the adaptive bio-signal feature combining apparatus 800 may repeatedly perform operations 1910 to 1940 to periodically update a combining coefficient of a first feature and a combining coefficient of a second feature according to a designated update period as shown in FIG. 9.

According to another exemplary embodiment, the adaptive bio-signal feature combining apparatus 800 may repeatedly perform operations 1910 to 1940 to constantly update the combining coefficient of the first feature and the combining coefficient of the second feature by overlapping at least one stable interval in a sliding-window scheme, as shown in FIG. 10.

Figure 20:
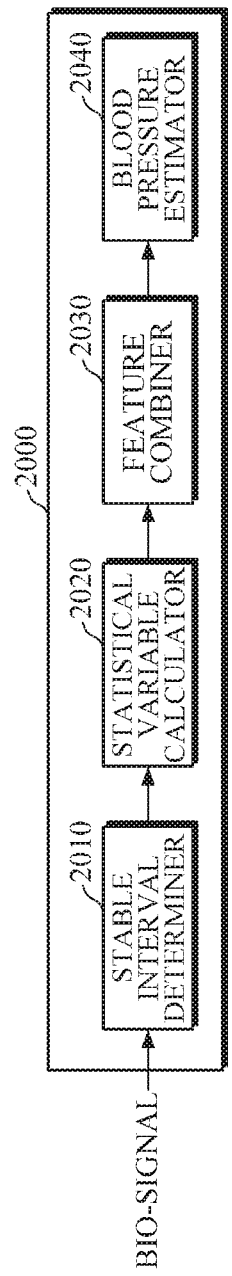
FIG. 20 is a block diagram illustrating a blood pressure measurement apparatus according to an exemplary embodiment.

FIG. 20 is a block diagram illustrating one embodiment of a blood pressure measurement apparatus.

Referring to FIG. 20, the blood pressure measurement apparatus 2000 includes a stable interval determiner 2010, a statistical variable calculator 2020, a feature combiner 2030, and a blood pressure estimator 2040. Here, the stable interval determiner 2010, the statistical variable calculator 2020, and the feature combiner 2030 may operate in substantially the same manner as the stable interval determiner 210, the statistical variable calculator 230, and the feature combiner 240, respectively, and thus detailed descriptions thereof will be omitted.

The blood pressure estimator 2040 may estimate a blood pressure of an object based on the combined feature. In particular, the blood pressure estimator 2040 may use Equation 22.

$$\text{Blood Pressure} = af_{comb} + b \qquad (22)$$

Here, a denotes a scale factor and b denotes an offset. a and b may be calculated in advance using a statistical scheme or through a calibration process. $f_{comb}$ may be calculated using Equation 10 to Equation 12 or Equation 16 to Equation 18.

According to the exemplary embodiments, a blood pressure measurement apparatus may estimate a blood pressure level from a PPG bio-signal (e.g., a sum of a propagation wave 110 and reflection waves 120 to 150), even without using reference blood pressure levels. In order to estimate the blood pressure level, the blood pressure measurement apparatus may calculate a statistical variable of each of a plurality of features obtained from stable intervals of the PPG bio-signal, derive a feature combining coefficient based on the statistical variable, and linearly combine the features based on the feature combining coefficient. According to the blood pressure measurement apparatus, the blood pressure level is estimated adaptively in accordance with time and user changes, unlike in a related-art method of a blood pressure estimation that uses linear regression which requires a reference blood pressure level. According to the related-art method, the reference blood level needs to be updated or re-obtained when users are changed so that the reference blood level reflects unique biological characteristics of a new user.

FIG. 21 is a flowchart illustrating a blood pressure measurement method according to an exemplary embodiment.

The blood pressure measurement method of FIG. 21 may be performed by the blood pressure measurement apparatus 1700 of FIG. 20. Here, operations 2110 to 2140 may be substantially the same as operations 1420 to 1450 of FIG. 14, and thus detailed descriptions thereof will be omitted.

In operation 2150, the blood pressure measurement apparatus 2000 may estimate a blood pressure of an object based on a combined feature. At this time, the blood pressure measurement apparatus 2000 may use Equation 22.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An adaptive bio-signal feature combining apparatus comprising at least one processor configured to:
    continuously extract a first feature indicating a cardiac output (CO) and a second feature indicating a total peripheral vascular resistance (TPVR), from a photoplethysmogram (PPG) signal of an object in a non-resting state, while the PPG signal is continuously being measured;
    determine at least two stable intervals in the PPG signal, during which the object remains in a resting state, wherein the at least two stable intervals comprise a first stable interval and a second stable interval;
    obtain a first statistical variable value of the first feature and a second statistical variable value of the second feature, based on transient changes in the first feature and the second feature that are continuously extracted during the first stable interval and the second stable interval, respectively;
    obtain an integrated combining coefficient by averaging a first combining coefficient that represents a ratio between the first statistical variable value and the second statistical variable value during the first stable interval, and a second combining coefficient that represents a ratio between the first statistical variable value and the second statistical variable value during the second stable interval; and
    estimate a blood pressure of the object by combining the first feature and the second feature using the integrated combining coefficient.

2. The adaptive bio-signal feature combining apparatus of claim 1, wherein the first feature comprises at least one of $P_{max}/P_{area}$, $P_{max}/P_3$, $P_{sys}/P_3$, $P_1/P_3$, $P_2/P_3$, and $1/T_{period}$, the second feature comprises at least one of $1/(T_3-T_{sys})$, $1/(T_3-T_{max})$, $1/(T_3-T_1)$, $1/(T_3-T_2)$, $P_2/P_1$, and $P_3/P_1$, wherein $T_{period}$ denotes a period of the PPG signal, $T_1$ denotes a time of a peak point of a first component pulse constituting the PPG signal, $P_1$ denotes an amplitude of the PPG signal at $T_1$, $T_2$ denotes a time of a peak point of a second component pulse constituting the PPG signal, $P_2$ denotes an amplitude of the PPG signal at $T_2$, $T_3$ denotes a time of a peak point of a third component pulse constituting the PPG signal, $P_3$ denotes an amplitude of the PPG signal at $T_3$, $T_{max}$ denotes a time of a peak point of the PPG signal, $P_{max}$ denotes an amplitude of the PPG signal at $T_{max}$, $T_{sys}$ denotes an intermediate time between $T_1$ and $T_{max}$, an arbitrary internally dividing point between $T_1$ and $T_{max}$, or an arbitrary internally dividing point between $T_1$ and $T_2$, $P_{sys}$ denotes an amplitude of the PPG signal at $T_{sys}$, and $P_{area}$ denotes a sum of amplitudes of the PPG signal.

3. The adaptive bio-signal feature combining apparatus of claim 1, wherein the at least one processor is further configured to determine the at least two stable intervals based on an output value of a sensor that detects a motion of the object.

4. The adaptive bio-signal feature combining apparatus of claim 3, wherein the at least one processor is further configured to compare the output value of the sensor at a time of bio-signal measurement with a predetermined threshold value, and in response to the output value of the sensor being maintained less than or equal to the predetermined threshold value for a predetermined time period, determine that the predetermined time period is the at least two stable intervals.

5. The adaptive bio-signal feature combining apparatus of claim 1, wherein the at least one processor is further configured to determine the at least two stable intervals based on an amount of change in the first feature or the second feature extracted from the PPG signal.

6. The adaptive bio-signal feature combining apparatus of claim 5, wherein the amount of change in the first feature or the second feature is defined as a fluctuation with respect to a mean value of the first feature or the second feature.

7. The adaptive bio-signal feature combining apparatus of claim 6, wherein the fluctuation comprises a variance, a standard deviation, and a mean absolute deviation.

8. The adaptive bio-signal feature combining apparatus of claim 5, wherein the at least one processor is further configured to compare the amount of change in the first feature or the second feature extracted during a time period with a predetermined threshold value, and determine the time period as the at least one stable intervals when the amount of change in the first feature or the second feature is less than or equal to the predetermined threshold value.

9. The adaptive bio-signal feature combining apparatus of claim 1, wherein the first statistical variable corresponds to a mean, a variance, a standard deviation, of a mean absolute deviation of values of the first feature that change during the at least two stable intervals.

10. The adaptive bio-signal feature combining apparatus of claim 1, wherein the at least one processor is further configured to calculate the integrated combining coefficient by dividing the first statistical variable value by the second statistical variable value of each of the at least two stable intervals.

11. The adaptive bio-signal feature combining apparatus of claim 1, wherein the at least one processor is further configured to calculate the integrated combining coefficient by arithmetically averaging individual combining coefficients calculated for each of the at least two stable intervals.

12. The adaptive bio-signal feature combining apparatus of claim 1, wherein the at least one processor is further configured to calculate the integrated combining coefficient by applying different weights to individual combining coefficients calculated for each stable interval and linearly combining the individual combining coefficients to which the different weights are applied.

13. The adaptive bio-signal feature combining apparatus of claim 12, wherein the at least one processor is further configured to apply a higher weight to an individual combining coefficient of a temporally later stable interval, among the individual combining coefficients for the at least two stable intervals.

14. The adaptive bio-signal feature combining apparatus of claim 1, wherein the at least one processor is further configured to linearly combine the first feature and the second feature based on the integrated combining coefficient.

15. The adaptive bio-signal feature combining apparatus of claim 1, wherein the at least one processor is further configured to update the integrated combining coefficient.

16. The adaptive bio-signal feature combining apparatus of claim 15, wherein the at least one processor is further configured to update the integrated combining coefficient according to a designated update period.

17. The adaptive bio-signal feature combining apparatus of claim 15, wherein the at least one processor is further configured to constantly update the integrated combining coefficient by overlapping the at least two stable intervals in a sliding-window scheme.

18. The adaptive bio-signal feature combining apparatus of claim 1, wherein the at least one processor is further configured to:
calculate a covariance between the first feature and the second feature,
calculate the integrated combining coefficient based on the first statistical variable value, the second statistical variable value, and the covariance.

19. The adaptive bio-signal feature combining apparatus of claim 18, wherein the at least one processor is further configured to calculate the integrated combining coefficient based on the first statistical variable value, the second statistical variable value, and a correlation coefficient between the first feature and the second feature.

20. An adaptive bio-signal feature combining method comprising:
continuously extracting a first feature and a second feature, from a photoplethysmogram (PPG) signal of an object in a non-resting state, while continuously measuring the PPG signal;
determining at least two stable intervals in the PPG signal, during which the object remains in a resting state, wherein the at least two stable intervals comprise a first stable interval and a second stable interval;
obtaining a first statistical variable value of the first feature and a second statistical variable value of the second feature, based on transient changes in the first feature and the second feature which are continuously extracted during the first stable interval and the second stable interval, respectively;
obtaining an integrated combining coefficient by averaging a first combining coefficient that represents a ratio between the first statistical variable and the second statistical variable during the first stable interval, and a second combining coefficient that represents a ratio between the first statistical variable value and the second statistical variable value during the second stable interval; and estimating a blood pressure of the object by combining the first feature and the second feature using the integrated combining coefficient.

* * * * *